(12) United States Patent
Gunter et al.

(10) Patent No.: US 7,894,126 B2
(45) Date of Patent: Feb. 22, 2011

(54) BROADBAND TERAHERTZ RADIATION GENERATION AND DETECTION SYSTEM AND METHOD

(75) Inventors: Peter Gunter, Riedt-Neerach (CH); Arno Schneider, Zurich (CH)

(73) Assignee: ETH Zurich, Zurich (CH)

( * ) Notice: Subject to any disclaimer, the term of this patent is extended or adjusted under 35 U.S.C. 154(b) by 0 days.

(21) Appl. No.: 12/297,721

(22) PCT Filed: Apr. 18, 2007

(86) PCT No.: PCT/CH2007/000184
§ 371 (c)(1),
(2), (4) Date: Jan. 20, 2009

(87) PCT Pub. No.: WO2007/121598
PCT Pub. Date: Nov. 1, 2007

(65) Prior Publication Data
US 2009/0303574 A1    Dec. 10, 2009

Related U.S. Application Data

(60) Provisional application No. 60/794,013, filed on Apr. 21, 2006.

(51) Int. Cl.
G02F 1/355 (2006.01)
G02F 1/35 (2006.01)
(52) U.S. Cl. .................... 359/328; 359/326; 372/22; 372/105
(58) Field of Classification Search ......... 359/326–332; 372/21, 22, 98, 105; 385/122
See application file for complete search history.

(56) References Cited

U.S. PATENT DOCUMENTS 6,723,991 B1 * 4/2004 Sucha et al. ............. 250/341.1

(Continued)

FOREIGN PATENT DOCUMENTS

GB    2417554 A    3/2006

OTHER PUBLICATIONS

Ferguson, B. et al.; "Materials for terahertz science and technology," Nature Materials; vol. 1; pp. 26-33; Nature Publishing Group; Sep. 2002.

(Continued)

*Primary Examiner*—Daniel Petkovsek
(74) *Attorney, Agent, or Firm*—Rankin, Hill & Clark LLP

(57) ABSTRACT

The invention relates to a broadband Terahertz (THz) radiation generation and detection system and method. THz radiation is generated by optical rectification of an ultrashort pump pulse of a first wavelength having a duration in the picosecond- or sub-picosecond range in a first nonlinear optical crystal. The THz radiation is detected by electro-optic sampling or another appropriate method of a probe beam having a second wavelength in a second nonlinear optical crystal. According to the invention, at least one of the following conditions is fulfilled: a) the first wavelength is different from the second wavelength; b) the material of the first nonlinear optical crystal is different from the material of the second nonlinear optical crystal. This makes it possible to choose for the generation and for the detection process—independent of one another—the combination of wavelengths and nonlinear material and possibly other features of the pump/probe pulses like polarization with the highest efficiency for generation and detection of Terahertz pulses, respectively.

31 Claims, 16 Drawing Sheets

U.S. PATENT DOCUMENTS 6,957,099 B1 10/2005 Arnone et al.
7,718,969 B2 * 5/2010 Zhang et al. ............. 250/341.8

OTHER PUBLICATIONS

Nahata, A; et al.; "A wideband coherent terahertz spectroscopy system using optical rectification and electro-optic sampling," Applied Physics Letters; vol. 69, No. 16; pp. 2321-2323; American Institute of Physics; Oct. 14, 1996.

Wu, Q. et al.; "Design and Characterization of Traveling-Wave Electrooptic Terahertz Sensors," IEEE Journal of Selected Topics in Quantum Electronics; vol. 2 No. 3; pp. 693-700; Sep. 1996.

Nagai, M. et al.; "Generation and detection of terahertz radiation by electro-optical process in GaAs using 1.26 [μ]m fiber laser pulses"; Applied Physics Letters AIP USA; vol. 85, No. 18; Nov. 1, 2004; pp. 3974-3976; XP012063147.

Hayden, L.M. et al.; "New Materials for Optical Rectification and Electrooptic Sampling of Ultrashort Pulses in the Terahertz Regime," Journal of Polymer Science: Part B: Polymer Physics; vol. 41; pp. 2492-2500; Wiley Periodicals, Inc.; 2003.

Pan, F. et al.; "Electro- optic properties of the organic salt 4-N,N-dimethylamino-4'-N'-methyl-stilbazolium tosylate," Applied Physics Letters; vol. 69, No. 1; pp. 13-15; American Institute of Physics; Jul. 1, 1996.

Schneider, A. et al; "Optimized generation of THz pulses via optical rectification in the organic salt DAST"; Optics Communications, North-Holland Publishing Co.; Amsterdam, Netherlands; vol. 224, No. 4-6; Sep. 1, 2003; pp. 337-341; XP004454968.

Bakker, H.J. et al.; "Distortion of terahertz pulses in electro-optic sampling," Journal. Opt. Soc. Am. B; vol. 15, No. 6; pp. 1795-1801; Optical Society of America; 1998.

Wu, Q. et al.; "Free-space electro-optic sampling of terahertz beams," Applied Physics Letters; vol. 67, No. 24; pp. 3523-3525; American Institute of Physics; Dec. 11, 1995.

Han, P.Y. et al.; "Use of the organic crystal DAST for terahertz beam applications," Optics Letters; vol. 25, No. 9; pp. 675-677; Optical Society of America; May 1, 2000.

Wu, Q. et al.; "Two-dimensional electro-optic imaging of THz beams," Applied Physics Letters; vol. 69, No. 8; pp. 1026-1028; American Institute of Physics; Aug. 19, 1996.

Shan, J. et al.; "Single-shot measurement of terahertz electromagnetic pulses by use of electro-optic sampling," Optics Letters; vol. 25, No. 6; pp. 426-428; Optical Society of America; Mar. 15, 2000.

Walther, M. et al.; "Far-infrared properties of DAST," Optics Letters; vol. 25, No. 12; pp. 911-913; Optical Society of America; Jun. 15, 2000.

Schneider, A. et al.; "Generation of terahertz pulses through optical rectification in organic DAST crystals: Theory and experiment," J. Opt. Soc. Am. B; vol. 23, No. 9; pp. 1822-1835; Sep. 2006.

Gallot, G. et al.; "Measurements of the THz absorption and dispersion of ZnTe and their relevance to the electro-optic detection of THz radiation," Applied Physics Letters; vol. 74, No. 23; pp. 3450-3452; American Institute of Physics; Jun. 7,1999.

Schall, M. et al.; "Fundamental and second-order phonon processes in CdTe and ZnTe," Physical Review B; vol. 64; pp. 094301-1 to 094301-8; The American Physical Society; 2001.

Sliker, T.R. et al.; "Linear Electro-Optic Effect and Refractive Indices of Cubic ZnTe," Journal of the Optical Society of America; vol. 56; No. 1; pp. 130-131; Jan. 1966.

Sato, K. et al.; "Optical properties of ZnTe," Journal of Applied Physics; vol. 73, No. 2; pp. 926-931; American Institute of Physics; Jan. 15, 1993.

Schneider, Arno et al.; "Terahertz-induced lensing and its use for the detection of terahertz pulses in a birefringent crystal"; Applied Physics Letters; AIP; American Institute of Physics; Melville, New York, USA; vol. 84, No. 13; Mar. 29, 2004; pp. 2229-2231; XP012060888.

Taniuchi, T. et al.; "Widely tunable terahertz-wave generation in an organic crystal and its spectroscopic application"; Journal of Applied Physics, American Institute of Physics; New York, USA; vol. 95, No. 11; Jun. 1, 2004; pp. 5984-5988; XP012066680.

Yang, Z. et al.; "Large-size bulk and thin-film stilbazolium-salt single crystals for nonlinear optics and THz generation," Advanced Functional Materials; vol. 17; pp. 2018-2023; Wiley-VCH Verlag GmBH & Co. KGaA; 2007.

Yang, Z. et al.; "Synthesis and Crystal Growth of Stilbazolium Derivatives for Second-Order Nonlinear Optics," Advanced Functional Materials; vol. 15; pp. 1072-1076; Wiley-VCH Verlag GmBH & Co. KGaA; 2005.

Ruiz, B. et al.; "Synthesis and crystal structure of a new stilbazolium salt with large second-order optical nonlinearity," Journal of Materials Chemistry; vol. 16; pp. 2839-2842; the Royal society of Chemistry; 2006.

* cited by examiner

BROADBAND TERAHERTZ RADIATION GENERATION AND DETECTION SYSTEM AND METHOD This application claims priority from U.S. provisional patent application No. 60/794,013 filed Apr. 21, 2006. For the United States of America, this is a regular patent application based on this U.S. provisional No. 60/794,013.

BACKGROUND OF THE INVENTION

1. Field of the Invention

The invention relates to the generation and detection of Terahertz (THz) radiation, and more specifically to the generation and detection of pulsed Terahertz (THz) radiation in nonlinear optical crystals pumped by ultrashort optical pulses.

2. Description of Related Art

In the past decade, the science and technology on electromagnetic radiation with a spectral content in the 0.1 to 10 THz range (Terahertz or THz radiation, 1 THz=$10^{12}$ $s^{-1}$) have attracted widespread interest and evolved into a useful tool for a number of applications (see Ref. [1] for a review). Many materials are transparent for electromagnetic radiation in the THz range, but unlike X-rays the THz radiation does not have an ionizing effect on the material due to the low energy of its photons. This makes it possible to apply THz radiation in different areas such as imaging of biological tissue and the measurement of fundamental solid-state processes in semiconductor physics.

For some applications, namely THz absorption spectroscopy or spectroscopic imaging, tunable narrow-band THz pulses with nanosecond duration may be favorable due to their better spectral resolution. Such systems for generating narrow-band THz radiation with a well defined THz frequency by means of difference frequency generation in a nonlinear optical crystal are known, e.g. from U.S. Pat. No. 7,054,339. A pair of fiber lasers generates single-frequency outputs at frequencies $\omega 1$ and $\omega 2$. The nonlinear interaction process in the nonlinear optical crystal generates THz radiation at $\Omega=\omega 1-\omega 2$ (difference frequency generation, DFG). These systems are complicated because they need two lasers that have to be synchronized and combined.

For some applications it is desirable to have shorter THz pulses, e.g. in the picosecond ($10^{-12}$ s) or sub-picosecond range. Such broadband THz pulses on a picosecond time scale offer additional benefits that are unique to this technique. The excellence of such broadband THz pulses is the possibility of a phase-coherent detection technique that provides the inherent advantage of a time-resolution that may be as short as a few tens of femtoseconds ($10^{-15}$ s).

Broadband THz pulses may be generated by several methods which all employ femtosecond laser pulses, namely using photoconductive switches, semiconductor surfaces, and optical rectification (OR) in nonlinear optical crystals. A pump pulse in the picosecond or sub-picosecond range contains frequencies in a frequency band $\Delta\omega$ around the central frequency $\omega$. Such an ultrashort pulse may produce broadband electromagnetic radiation at THz frequencies in a nonlinear optical material if certain phase matching and velocity matching conditions are fulfilled. This process is known as optical rectification.

A frequently used technique for the coherent detection of THz pulses is electro-optic (EO) sampling, a process that is based on the interaction of an optical pulse with the THz wave in a nonlinear material. A THz pulse traveling through the crystal is able to change the polarization of a co-propagating probe pulse in the optical range. This change of polarization is a measure for the electric field of the THz pulse and can be detected by appropriate means, e.g. a polarization beam splitter in combination with two photodetectors. EO sampling enables coherent detection of the THz pulse.

Among different approaches to generate and coherently detect THz pulses, which all require femtosecond lasers, those based on nonlinear optical effects (optical rectification (OR) and electro-optic (EO) sampling, respectively [2]) are advantageous since they use optical pulses at wavelengths outside the material's absorption range. Therefore the emitted THz field scales with both optical pulse energy and source crystal thickness up to the coherence length (see Eq. (2)), whereas the THz emission from processes that involve the excitation of free charge carriers (e.g. in photoconductive switches) is limited to the optical absorption length of the optical radiation; furthermore there is a risk of damaging the source through high optical power in the latter case.

Two prerequisites are given for a nonlinear optical material to be useful for THz applications, especially THz generation via OR and detection via EO sampling. First is a sufficient nonlinear optical susceptibility $X^{(2)}$ and electro-optic (EO) coefficient r. Second is velocity-matching between the optical and the THz pulse, i.e. the THz and the optical pulse have to propagate through the crystal with the same velocity. Velocity-matching is characterized by the coherence length $l_c$; the latter ought to be at least the crystal thickness, typically 0.1 to 1 mm. Due to dispersion, $l_c$ is a function of both the optical wavelength $\lambda$ and the THz frequency v. Hence, the material of choice depends on the desired range of v and the available laser source.

Velocity-matching with THz pulses is achieved e.g. within the inorganic semiconductor ZnTe (zinc telluride) when one uses laser pulses at a wavelength of, for example, 822 nm, i.e., within the tuning range of the widely used Ti:sapphire femtosecond lasers. This factor made ZnTe the material of choice for the generation of pulses with a broadband spectrum below a frequency of 3 THz. ZnTe has an electro-optic coefficient r=4 pm/V and good velocity-matching between optical pulses from Ti:Sapphire lasers also at $\lambda<800$ nm [3]. Ti:Sapphire lasers, however, are still very complex, require a given space and maintenance and are costly.

Among inorganic semiconductors, GaAs with an optimum velocity-matching wavelength of 1.4 μm [3] is the most promising candidate for generation and detection with "telecommunication" wavelengths (around 1.5 μm) and has been demonstrated as a source and detection material with 1.56 μm pulses from a fiber laser [4]. However, its electro-optic (EO) coefficient is about a factor of two lower than that of ZnTe.

Generally, organic nonlinear optical materials offer several advantages for THz applications, namely their high nonlinear optical susceptibilites, low dielectric constants, and the almost unlimited possibility to design molecules for a specific application [5]. These molecules can be incorporated in either organic crystals or polymers. Although polymers may be efficient emitters and detectors of THz radiation [6], they suffer from fast degradation and limited thickness; disadvantages that apply for organic crystals to a much lesser extent.

A known organic nonlinear optical material suited for the generation of THz pulses is the crystal DAST (4-N,N-dimethylamino-4'-N'-methyl stilbazolium tosylate). The EO coefficient of DAST ($r_{111}$=47 pm/V at $\lambda$=1535 nm [7]) is more than an order of magnitude higher than that of ZnTe or GaAs. Velocity-matching between THz pulses and optical pulses with a wavelength $\lambda$ around 1300 nm in DAST has been observed [8],[20]. Therefore, THz generation with a high conversion efficiency in DAST is possible. However, the coherent detection by EO sampling in DAST is problematic as DAST has a high birefringence and is thus not suited for EO sampling.

Ref. [20] proposes to employ another effect, namely the focusing of the probe beam ("Terahertz induced lensing", TIL) by a spatial variation of the refractive index of the DAST crystal caused by a co-propagating THz pulse. The change in the beam profile can be detected, e.g. by measuring the intensity at a certain location of a screen onto which the optical probe beam is directed. The detection via TIL, however, may have a reduced sensitivity as compared to EO sampling in ZnTe if the relevant electro-optical coefficients are the same.

It is, therefore, an objective of the invention to provide a system and a method for broadband THz generation and detection that has an increased conversion efficiency in the generation step and an increased sensitivity in the detection step.

It is a further objective of the invention to provide a system and a method for broadband THz generation and detection that has a reduced complexity, does not require permanent maintenance and attention and is thus suited for commercial use, e.g. as a THz spectrometer and/or imaging device.

BRIEF SUMMARY OF THE INVENTION

These and other objects are achieved by a broadband Terahertz radiation generation and detection system. Preferred embodiments are described in the dependent claims and in the following description.

The inventive system includes a light source for generating a pump beam and a probe beam, each including light pulses in the optical range (including UV, visible and infrared light) having a pulse duration in the picosecond- or sub-picosecond range, wherein said pump beam has a first wavelength ($\lambda 1$) and said probe beam has a second wavelength ($\lambda 2$), that may be identical to the first wavelength or different therefrom. The system further includes a first nonlinear optical crystal arranged in the path traveled by the pump beam (pump beam path). The optical properties of the first nonlinear optical crystal are chosen such that Terahertz pulses forming a Terahertz beam are generated when the pump beam travels through the first nonlinear optical crystal, e.g. by optical rectification. The Terahertz beam travels along a Terahertz beam path. The system further includes a second nonlinear optical crystal arranged in the path traveled by the probe beam (probe beam path). The optical properties of the second nonlinear optical crystal are chosen such that optical properties of the probe beam are altered, e.g. by EO sampling or TIL, when the second nonlinear optical crystal is exposed with the probe beam and the Terahertz beam. In the region of the second nonlinear optical crystal, the beam paths of the probe beam and the Terahertz beam are, thus, partially aligned. The system further includes detection means for detecting predetermined optical parameters of the probe beam, e.g. its polarization and/or intensity. According to the invention, at least one of the following conditions is fulfilled: a) the first wavelength (wavelength of the pump beam) is different from the second wavelength (wavelength of the probe beam); b) the material of the first nonlinear optical crystal used for the generation of THz pulses is different from the material of the second nonlinear optical crystal used for the detection of THz pulses.

The ultrashort probe and THz pulses enable coherent detection of the THz radiation. This makes it possible to gain time-resolved and/or spectral information on a sample.

The system may further include beam path shaping means, e.g. normal or dichroic mirrors, normal or polarization beam splitters, lenses and the like, to shape the beam paths in the desired way. A sample is preferably arranged in the Terahertz beam path at a location before the second nonlinear optical crystal.

The light source can include a single light emitting element, preferably a laser, in combination with adequate means, e.g. beam splitters, frequency doubling, for generating the probe beam and the pump beam at different wavelengths or the same wavelength. As an alternative, the light source can include multiple light emitting elements, e.g. two synchronized lasers, that generate the pump beam and the probe beam, respecitvely.

The light source is preferably able to generate pairs of ultrashort pulses at first and second wavelengths that may be the same or different from one another. The light source preferably includes a laser. The light source is, for example, a laser having an output at the first wavelength—used as pump beam—in combination with a frequency doubling means, e.g. a nonlinear crystal like BBO, $LiNbO_3$, $KNbO_3$, for generating the second harmonic of the first wavelength that is then used as a probe beam. This embodiment will be described in more detail below. The light source may also be an optical parametric amplifier (OPA) or optical parametric oscillator (OPO) generating a signal and idler beam with constant sum-of-frequencies. The signal beam may be used as pump beam, and the idler beam as probe beam, or vice versa. Other nonlinear processes may be employed as well, e.g. third harmonic generation and the like. It is also possible that pump beam and probe beam have the same wavelength; in this case, the light source may simply be a laser with a beam splitter to split the probe beam from the pump beam.

As the pump and probe pulses have a duration in the picosecond or sub-picosecond range, they have a certain bandwidth of wavelengths. This bandwidth determines the upper frequency of the achievable THz spectrum. In the context of the present invention, the first and second wavelengths are the central wavelengths of the pump and probe pulses.

The system may also include a delay arranged in one of the beam paths. This delay serves to adapt the lengths of the respective beam paths to one another and ensures that the Terahertz pulse and the probe pulse overlap (in time domain) within the second nonlinear crystal, such that the Terahertz pulse affects the probe pulse and coherent detection is possible. Furthermore, the shape of the Terahertz pulse can be probed by varying the delay, thus enabling coherent detection and access to spectral information of the Terahertz pulse.

The inventive method for broadband Terahertz generation and detection, includes the following steps:

generating a pump beam and a probe beam each including light pulses in the optical range having a pulse duration in the picosecond- or sub-picosecond range, wherein said pump beam has a first wavelength ($\lambda 1$) and said probe beam has a second wavelength ($\lambda 2$);

exposing a first nonlinear optical crystal with the pump beam in order to generate a Terahertz beam;

directing the Terahertz beam onto a sample;

exposing a second nonlinear optical crystal with the probe beam and the Terahertz beam in order to alter optical properties of the probe beam in presence of the Terahertz beam;

detecting predetermined optical parameters of the probe beam, wherein at least one of the following conditions is fulfilled:
a) the first wavelength ($\lambda 1$) is different from the second wavelength ($\lambda 2$); b) the material of the first nonlinear optical crystal is different from the material of the second nonlinear optical crystal.

The invention makes it possible to chose for the generation and for the detection—independent of one another—the combination of wavelengths and nonlinear material and possibly other features of the pump/probe pulses like polarization with the highest efficiency for generation and detection of Terahertz pulses, respectively. By using pairs of pump/probe pulses that originate from the same source (or from two very precisely synchronized sources) coherent detection is possible. Ultrashort pump pulses enable generation of broadband Terahertz pulses that contain a continous spectrum from 1.3 to 4.8 THz (in DAST), for example. The spectral content of these pulses, after passing a sample, can be resolved by coherent detection, giving a kind of fingerprint of the sample. Furthermore, time resolution as short as a few tens of femtoseconds is possible.

Generally, materials with a high nonlinear optical susceptibility in which velocity-matching between the generated Terahertz pulse and the pump pulse is given are suited for the generation of Terahertz pulses. Similarly, materials with a high nonlinear electro-optical coefficient or a high nonlinear optical susceptibility in which velocity-matching between the Terahertz pulse and the probe pulse is given are suited for the detection of Terahertz pulses.

The invention may be implemented by using already known and/or newly developed components. The combination of these components in the claimed way enables one to achieve an enhanced output that exceeds that of the Terahertz systems known so far. In particular, the invention makes it possible to use the high conversion efficiency achievable with organic nonlinear crystals in a first wavelength region, for example infrared, with the well established electro-optic sampling detection method in a different, second wavelength region, for example in the visible or infrared region.

Preferably, THz generation is achieved using a stilbazolium salt crystal. DAST (4-N,N-dimethylamino-4'-N'-methyl stilbazolium tosylate) has been described in the introductory portion of this application. Organic crystals, e.g. DAST derivatives like DSMOS (4-N,N-dimethylamino-4'-N'-methyl stilbazolium p-methoxybenzenesulfonate) [23] or DSTMS (4-N,N-dimethylamino-4'-N'-methyl stilbazolium 2,4,6 trimethylbenzenesulfonate) [22] or DSNS (4-N,N-dimethylamino-4'-N'-methyl-stilbazolium 2-naphthalenesulfonate) [24] with also very high nonlinear optical coefficients may be used as well.

Stilbazolium salt crystals, especially DAST, are effectively pumped with lasers emitting in the infrared range, e.g. between 1.0 and 1.7 µm, preferably between 1.3 and 1.6 µm, especially at telecommunication wavelengths from 1.5 to 1.56 µm. Effective THz generation in DAST is possible if the pump beam has a first wavelength between 1.4 and 1.7 µm and wherein the pump beam is directed onto the first nonlinear optical crystal such that its polarization is oriented along the main (a-) axis of the DAST crystal and the beam propagates in a direction in the b-c-plane. In this case, velocity-matching is achieved. Other orientations of the polarization vector with respect to the crystal axes are possible and lead to other pump wavelengths where velocity-matching is achieved.

It is further preferred that the THz detection is performed by electro-optic sampling in a second nonlinear optical crystal, e.g. ZnTe. Depending on the spectrum of the THz pulse, the preferred wavelength for the probe beam is, thus, around 800 nm. Other nonlinear detection materials like GaAs or GaP can be used as well. It is also possible to use a detection material in which Terahertz induced lensing (TIL) is observed, e.g. DAST.

Due to the progress in the telecommunications industry, compact and reliable and cost efficient femtosecond lasers, e.g. fiber lasers, emitting in the infrared wavelength range, e.g. from 1.5 to 1.56 µm, are becoming readily available. According to the invention, the detection process is independent of the generation process. The invention makes it, thus, possible to use these lasers to pump a nonlinear optical crystal, preferably DAST or a DAST derivative, for THz generation. The added value is that the wavelength range of these lasers allows an optimum efficiency of THz pulse generation in DAST crystals. Moreover, the variation of using a probe beam at another wavelength, in particular a frequency-doubled probe beam, allows the use of the well established and widely used material ZnTe also with optimum efficiency; additionally, electro-optic sampling is often more versatile than THz-induced lensing that had to be used before for detection when THz radiation was generated in DAST.

In a preferred embodiment, lasers emitting in the infrared range, in particular at telecom wavelengths, are used to generate THz radiation in DAST crystals, and the frequency doubled beam is used to coherently detect the THz radiation in a standard material like ZnTe.

The invention thus makes it possible to provide efficient, comparably compact, stable and cost-effective THz systems.

The invention is applicable, in particular, to systems using ultrashort THz pulses, namely for spectroscopic and imaging applications, e.g. for the security inspection of explosives, biothreats or materials testing, but not limited to these applications. Imaging applications have the appealing feature that besides the absorption also the sample thickness or the composition of a layered structure may be measured due to the coherent detection of the pulses.

When the variation of the delay is correlated with the measured THz amplitude, spectral information of the THz pulse—and indirectly also of a sample—can be retrieved.

In a preferred embodiment of the invention, few-cycle THz pulses are generated in the organic crystal DAST (4-N,N-dimethylamino-4'-N'-methyl stilbazolium tosylate) using a telecommunication wavelength in the range of 1.5 to 1.56 µm. A continuous spectrum from 1.3 to 4.8 THz was generated with a very high conversion efficiency ($E_{THz,max} < 50$ kV/cm at an optical pump pulse energy of 25 µJ in a 0.6 mm thick crystal) using the high nonlinear optical susceptibility of DAST ($X^{(2)}_{111} = 490$ pm/V at $\lambda = 1535$ nm) and velocity-matching observed in this material. Using a frequency-doubled probe beam at $\lambda = 750$ nm, nearly velocity-matched detection can also be realized in ZnTe crystals, resulting in a continuous spectrum from 1.3 to 4 THz.

For an orientation of the polarization such that the polarization vector has a component in the same direction as the b-axis of the crystal, in DAST also velocity-matching for other pump wavelengths is achievable, e.g. a first wavelength between 680 and 780 nm, preferably between 700 and 740 nm. Similar results can be expected for DAST derivatives. Further crystal orientations lead to other preferred pump wavelengths, e.g. a pump wavelength of 1000 and 1200 nm and orientation of the polarization vector in the ab-plane under 45° with respect to the a- and b-axis. Setups with such arrangements, e.g. as described in claims 10, 11, 27, and 28, have benefits also for efficient THz generation in general and may be used independent of the present invention. In the present invention, the THz generation in DAST or a DAST derivative with a first wavelength between 700 and 740 nm may be combined with detection in ZnTe at the same wavelength, for example, without the need for frequency doubling.

BRIEF DESCRIPTION OF THE DRAWINGS

FIG. 5a: Signal in time-domain. The indicated modulation is in first order proportional to the THz electric field, limited by nonlinear effects (see text for details).

FIG. 6a: Time-domain.

DESCRIPTION OF THE PREFERRED EMBODIMENTS

Introduction

Figure 1:
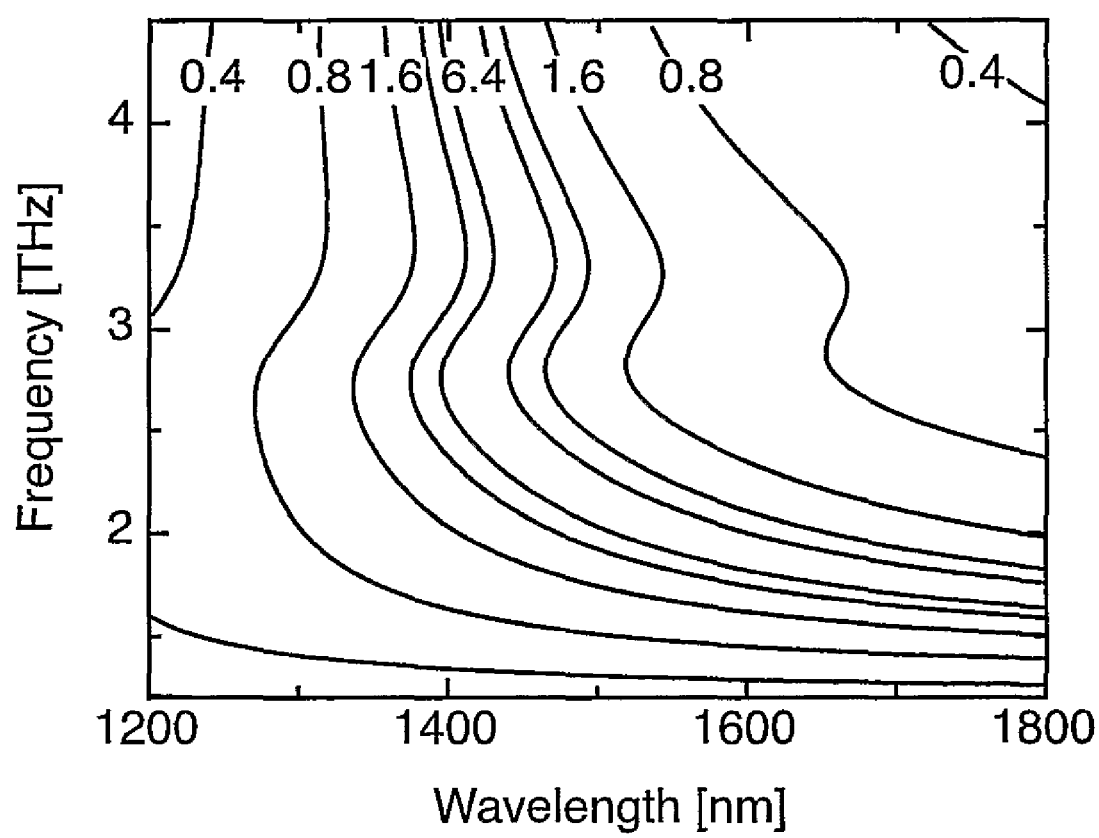
FIG. 1 shows a contour plot of the coherence length $l_c$ or THz generation and/or detection in DAST. The numbers indicate the value of the contour in millimeters.

The velocity-matched generation and detection of THz pulses with 1.5 µm laser pulses in the organic nonlinear crystal DAST (4-N,N-dimethylamino-4'-N'-methyl stilbazolium tosylate) with an EO coefficient ($r_{111}=47$ pm/V at $\lambda=1535$ nm [7]) that is more than an order of magnitude higher than that of ZnTe or GaAs is demonstrated theoretically and experimentally. A THz-induced modulation of up to 140% using a nominally linear technique is achieved (see section 4.1). Additionally, it is shown that DAST and ZnTe can be combined in a single THz system if one of the optical beams is frequency-doubled, which allows more versatile detection schemes.

Optimal wavelength range for generation/detection of THz pulses Optical rectification is a second-order nonlinear optical process, where two optical waves with angular frequency $\omega$ interact with each other in a noncentrosymmetric crystal to generate a dc polarisation $P_{OR}$ through the nonlinear susceptibility $X^{(2)}(\Omega=0; \omega,-\omega)$. If $P_{OR}$ is induced by a short laser pulse, i.e., with a typical duration of 200 fs or less, it contains components at angular frequencies $\Omega \neq 0$ that act as a source for radiation in the THz frequency range. This process may also be interpreted as the generation of the difference-frequency between the frequency components of the input pulse, thus using $X^{(2)}(\Omega; \omega,-\omega-\Omega)$. An upper limit for $\Omega$ is given approximately by the bandwidth $\Delta\omega$ of the optical pulse.

The efficiency of the THz pulse generation depends on the phase-matching between the optical and the THz wave. It can be characterized by a function $f(l, v, \lambda)$ that contains the complete dependence of the emitted THz electric field $E_{THZ}$ on the length l of the nonlinear crystal in the non-depleted pump approximation and in the absence of absorption [8]:

$$f(l, v, \lambda) = l\mathrm{sinc}\left[\frac{\pi}{2}\frac{l}{l_c(v, \lambda)}\right] \quad (1)$$

$v=\Omega/(2\pi)$ is the THz frequency, $\lambda=2\pi/\omega$ the optical wavelength, and $l_c(v, \lambda)$ the coherence length for THz generation. It has been pointed out that in the case of THz pulse generation, the optical group index $n_g(\lambda)$ rather than the refractive index $n(\lambda)$ determines the coherence length [2, 3, 9], in contrast to other nonlinear conversion processes such as second-harmonic generation (SHG). Thus $l_c(v, \lambda)$ is given by [2]

$$l_c(v, \lambda) = \frac{c}{2v|n_g(\lambda) - n(v)|} \quad (2)$$

with the group index $$n_g(\lambda) = n(\lambda) - \lambda\frac{\partial n}{\partial \lambda}\bigg|_\lambda \quad (3)$$

The coherent detection of the transient THz electric field $E_{THz}(t)$ through electro-optic sampling (EOS) [3, 10] is a prerequisite for the unique applications of these pulses. In standard EOS, $E_{THz}$ alters the polarisation state of a copropagating optical probe pulse through the linear electro-optic effect (Pockels effect). A measurement of this polarisation change as a function of the delay time between THz and probe pulse reveals the THz electric field $E_{THz}(t)$. The measured probe beam modulation also depends on the phase-matching conditions; for unequal propagation velocities of THz and probe pulse, the measured waveform gets distorted [9]. In the frequency-domain, the modulation amplitude is proportional to the same factor $f(l, v, \lambda)$ from Eq. (1) as the generation efficiency.

Maximizing f for a given THz frequency range by choosing the optical wavelength $\lambda$ and the crystal length l properly is thus necessary to obtain an optimal THz signal, in terms of both generation and detection. However, not all electro-optic materials are equally well suited for electro-optic sampling as for THz generation, since EOS in its standard configuration requires a material that is not or only weakly birefringent, which excludes e.g. DAST ($n_a - n_b = 0.53$ at $\lambda = 1.5$ μm). One possibility to overcome this restriction is a double-pass scheme [11], another is to use a variation of EOS that is not inhibited by the birefringence, namely THz-induced lensing (TIL) [8]. Nevertheless, standard EOS is more versatile since it allows extensions such as two-dimensional real-time imaging [12] or single-shot measurements [13]. According to the invention, a high-efficiency THz source using DAST is combined with the standard EOS detection in ZnTe in order to profit from the respective advantages.

2.1 DAST

In the following, we determine the THz frequency range where a long coherence length $l_c$ (Eq. (2)) allows efficient THz generation or detection for a given optical wavelength $\lambda$ in DAST in the $X^{(2)}_{111}$ configuration, i.e., both optical and THz waves are polarized along the crystal a-axis.

Walther et al. measured the refractive index $n_1(v)$ using THz time-domain spectroscopy from 0 to 3 THz [14]. We extended this range up to 4.2 THz using the same method [15]. Above a phonon resonance at 1.1 THz, $n_1(v)$ increases up to about 3 THz where it shows a small kink; above this frequency, it remains nearly constant. From 1.8 to 4.2 THz, it ranges between 2.2 and 2.3. These values match approximately the optical group index $n_{g,1}(\lambda)$ between 1.4 and 1.8 μm that was calculated analytically from the Sellmeier function determined by Pan et al. [7]. FIG. 1 shows a contour plot of the coherence length $l_c(v, \lambda)$ according to Eq. (2).

Broadband velocity-matching, i.e., a value of $l_c(v, \lambda)$ that is larger than a typical crystal thickness of 1 mm in a wide frequency range, is achieved for wavelengths $\lambda$ between 1.3 and 1.6 μm, with corresponding frequencies from 1.5 to above 4 THz. From these data it can be expected that telecommunication wavelengths (<1.50 to 1.56 μm) are well suited for pulsed THz systems that use DAST as the emitter material.

2.2 ZnTe

By comparing the THz transients measured with two ZnTe crystals of a different thickness, Wu et al. [3] found experimentally that broadband THz pulses with a frequency content below 2 THz are velocity-matched to optical pulses with $\lambda = 822$ nm. Due to THz dispersion, this wavelength changes with the center frequency of the THz pulse.

Figure 2:
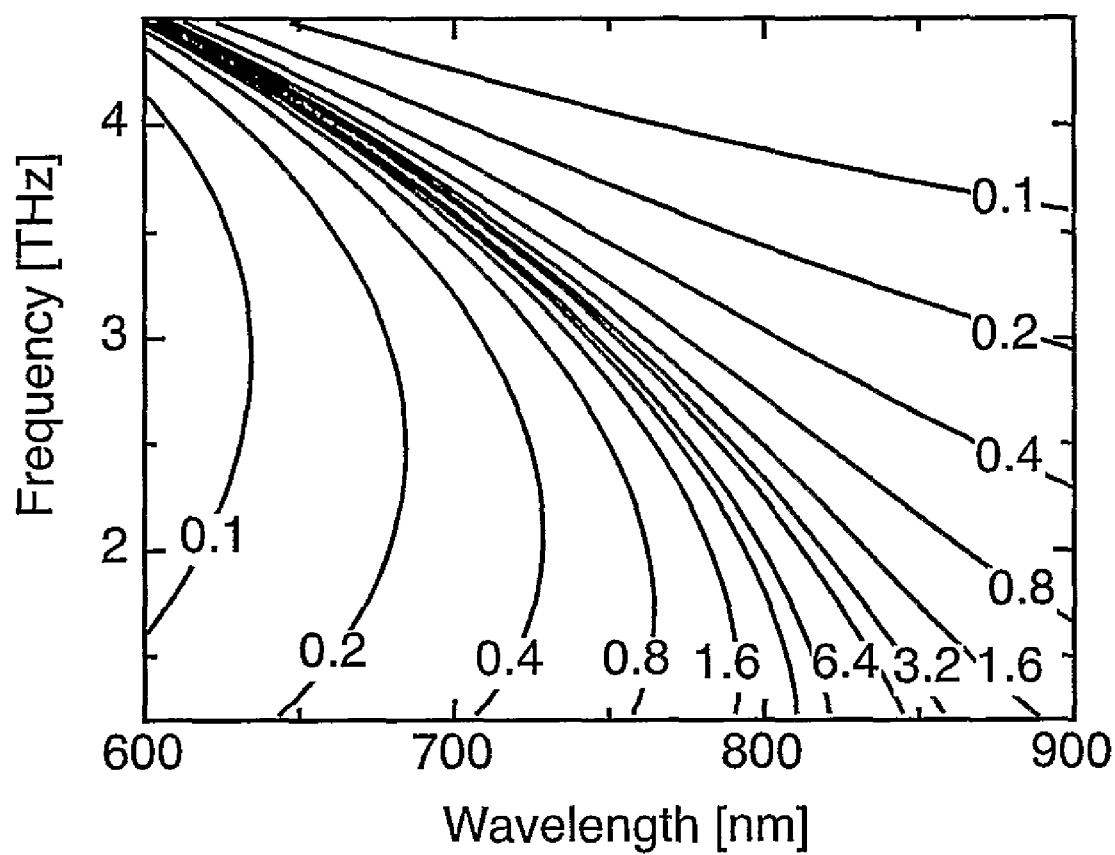
FIG. 2 shows a contour plot of the coherence length $l_c$ for THz generation and/or detection in ZnTe. The numbers indicate the value of the contour in millimeters.

For a quantitative analysis, we calculated the coherence length $l_c(v, \lambda)$ also for ZnTe. The result is shown in FIG. 2. The index data in the THz range are taken from references [16] and [17], those in the optical range are calculated with a Sellmeier fit to the data from Sliker et al. [18]; a more elaborate function for the optical dispersion of ZnTe presented by Sato et al. [19] does not agree better with the measured values in the 600-900 nm range and was therefore not used.

In the 2 to 3 THz range, the largest values of $l_c(v, \lambda)$ are obtained for wavelengths $\lambda$ between 750 and 850 nm (see FIG. 2), i.e., frequency-doubled pulses from lasers at telecom wavelengths may be used for velocity-matched electro-optic sampling in ZnTe.

Figure 3:
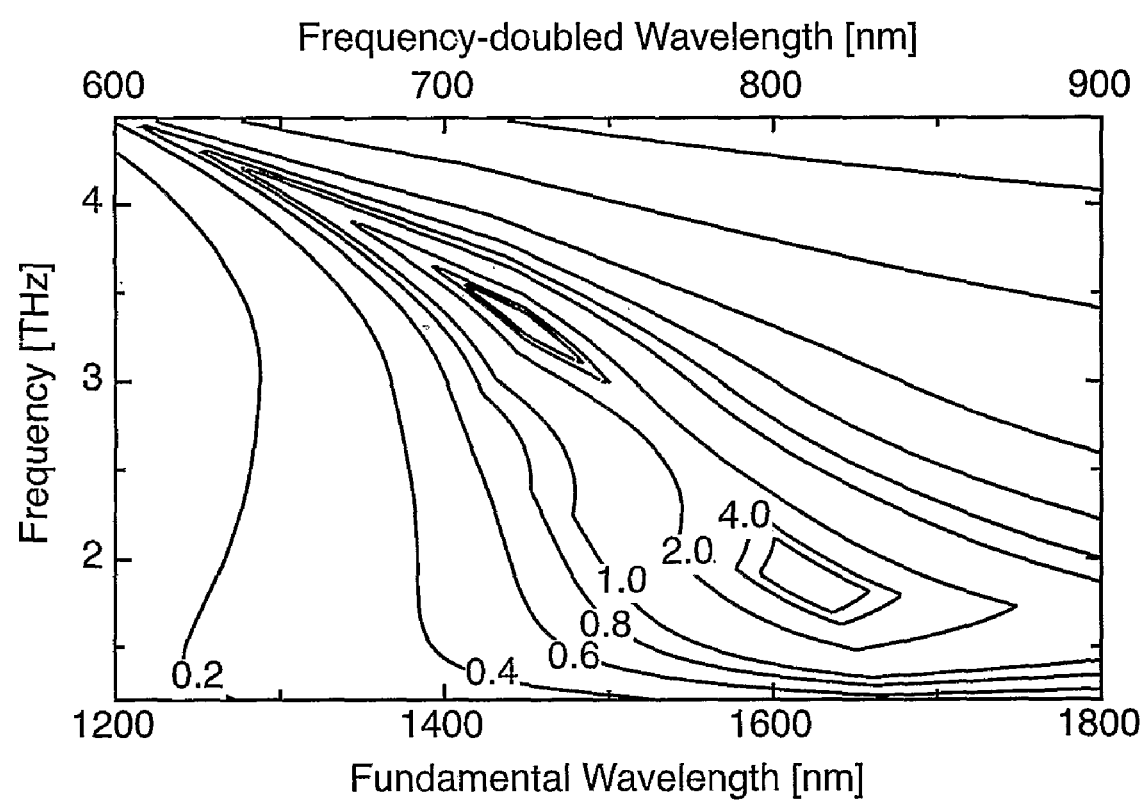
FIG. 3 shows a contour plot of the harmonic mean of the coherence lengths $l_c$ of DAST and ZnTe; the harmonic mean may serve as a measure for the efficiency of a THz system that combines two materials, one material for the generation and the other for the detection of the THz radiation.

Taking the results of the paragraphs 2.1 and 2.2, one finds that a THz spectroscopy or imaging system combining the advantages of highly efficient generation in DAST and velocity-matched EOS in ZnTe may be built using a telecom laser if the probe pulse is frequency-doubled. FIG. 3 resumes the data of FIG. 1 and FIG. 2 to show which combinations of THz frequency and optical wavelength are expected to give the highest detectable THz signal in a setup using DAST at the fundamental wavelength as the source and ZnTe at the frequency-doubled wavelength for the detection. One finds that the broadest THz frequency range is accessible with a fundamental wavelength near 1500 nm.

Experiments

The laser source in our experiment was an amplified Ti:Sapphire laser that generated pulses with a duration of 160 fs (full width at half maximum, FWHM) and a repetition rate of 1 kHz. Pulses in the desired wavelength range were obtained by means of an optical parametric generator/amplifier (OPG/OPA) whose signal wave was tunable from 1100 to 1600 nm, with a typical pulse energy of several tens of microjoules, depending on the wavelength. The signal wave with the angular frequency $\Omega$ was separated from the idler wave and the fundamental Ti:Sapphire wave by dichroic mirrors and appropriate filters.

Figure 4:
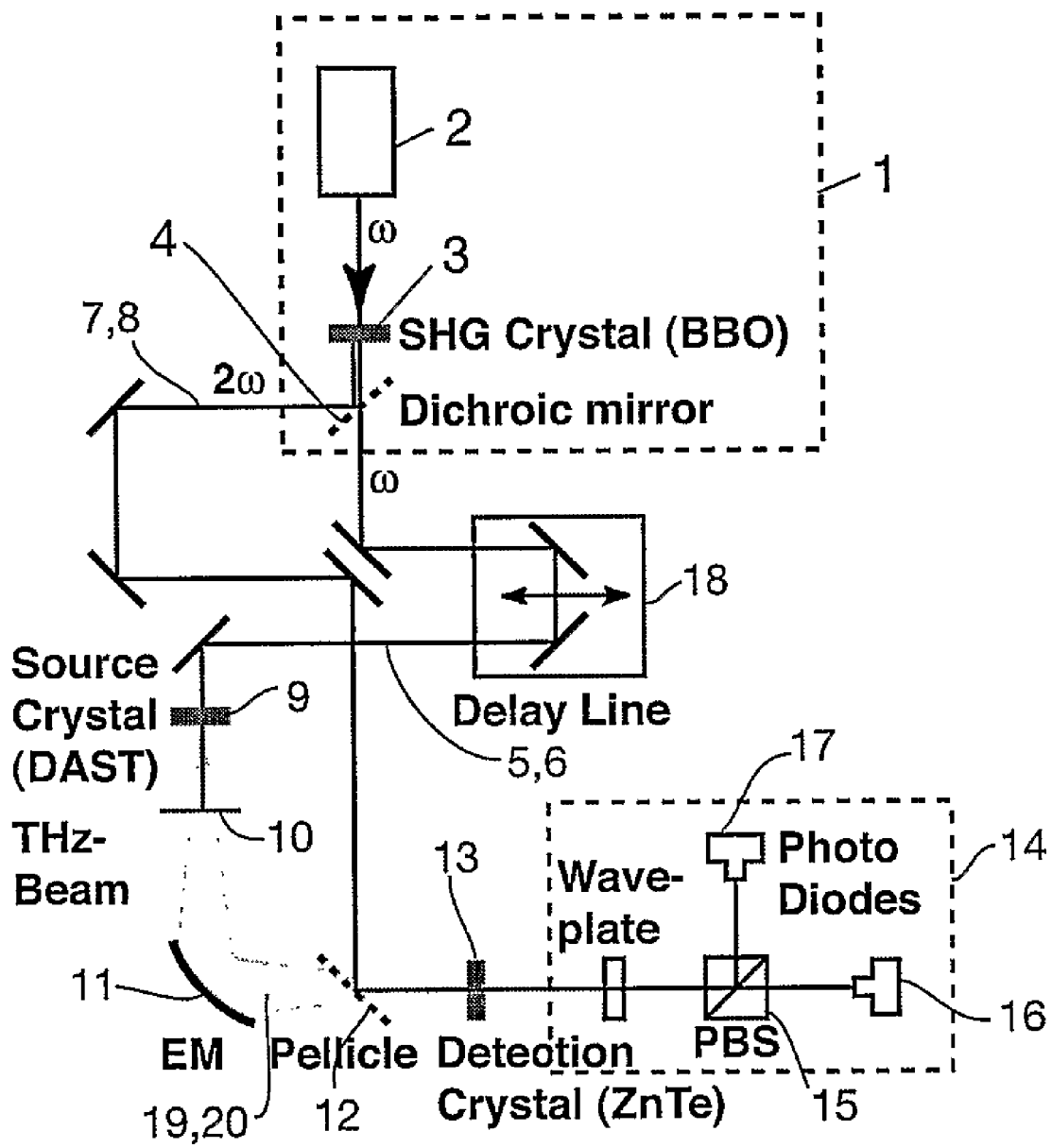
FIG. 4 shows the experimental setup using a pump beam at $\omega$ and a frequency-doubled probe beam at $2\omega$. EM: Ellipsoidal mirror; PBS: Polarizing Beam Splitter.

The setup that was used with a frequency-doubled probe beam is shown in FIG. 4. The light source 1 comprises a pulsed laser 2 and means 3 for generating a pump beam 5 and a probe beam 7 from the laser pulses. The incoming laser pulses at $\Omega$ pass a nonlinear optical crystal 3, here BBO, in which a fraction of the pulse energy is converted to the second-harmonic frequency $2\omega$. The two frequencies are then split by a dichroic mirror 4 into a pump pulse at the fundamental frequency $\Omega$ and a probe pulse at $2\omega$. Note that the energy of the probe pulse may be two to three orders of magnitude lower than that of the pump pulse since it only has to lead to an ample signal on the photodetectors 16, 17. Thus a high SHG conversion efficiency is not required, or even not desired, since a reduction of the pump pulse energy at the frequency $\Omega$ would decrease the emitted THz field.

The pump pulse or pump beam 5 travels a pump beam path 6, passing a delay line 18 with a variable delay (indicated by the arrows). The delay 18 may comprise one or more mirrors or may be an optical element that is able to induce a variable phase shift, e.g. a rotating plate with variable thickness. They then hit a first nonlinear optical crystal 9, here DAST, acting as source crystal for the THz radiation. The emitted THz beam 19 travels along a THz beam path 20. It is focused by a mirror 11 onto a second nonlinear optical crystal 13, here ZnTe, acting as detection crystal for the THz radiation. The pump beam 5 is blocked by an absorber 10 arranged behind the first nonlinear optical crystal 9 in the pump beam path 6.

The probe pulse or probe beam 7 travels along a probe beam path 8 to the second nonlinear optical crystal 13 and further to a detector 14. To combine the probe beam path 8 and the THz beam path 20, a pellicle 12 is used. As an alternative, other elements reflective for the optical beam and transmissive for THz radiation, or vice versa, can be used. The delay line 18 may be arranged in the probe beam path 8 instead of in the pump beam path 6.

The polarisation change that the electric field E of the THz pulse induced on the probe pulse in the electro-optic detection crystal 13 (ZnTe) is high enough to be measured directly by taking the ratio of the two polarisation components, split by a polarization beam splitter 15, by detecting their intensities with two photodiodes 16, 17, without the need of lock-in detection (which is also possible).

In the measurements with the probe beam at the fundamental frequency ω, the dichroic mirror 4 in FIG. 4 was replaced by a conventional beamsplitter 4'. The THz pulses were detected by THz-induced lensing in DAST as second nonlinear optical crystal 13 with the necessary changes in the detection setup 14 described in Ref. [20] and shown in FIG. 8.

Figure 8:
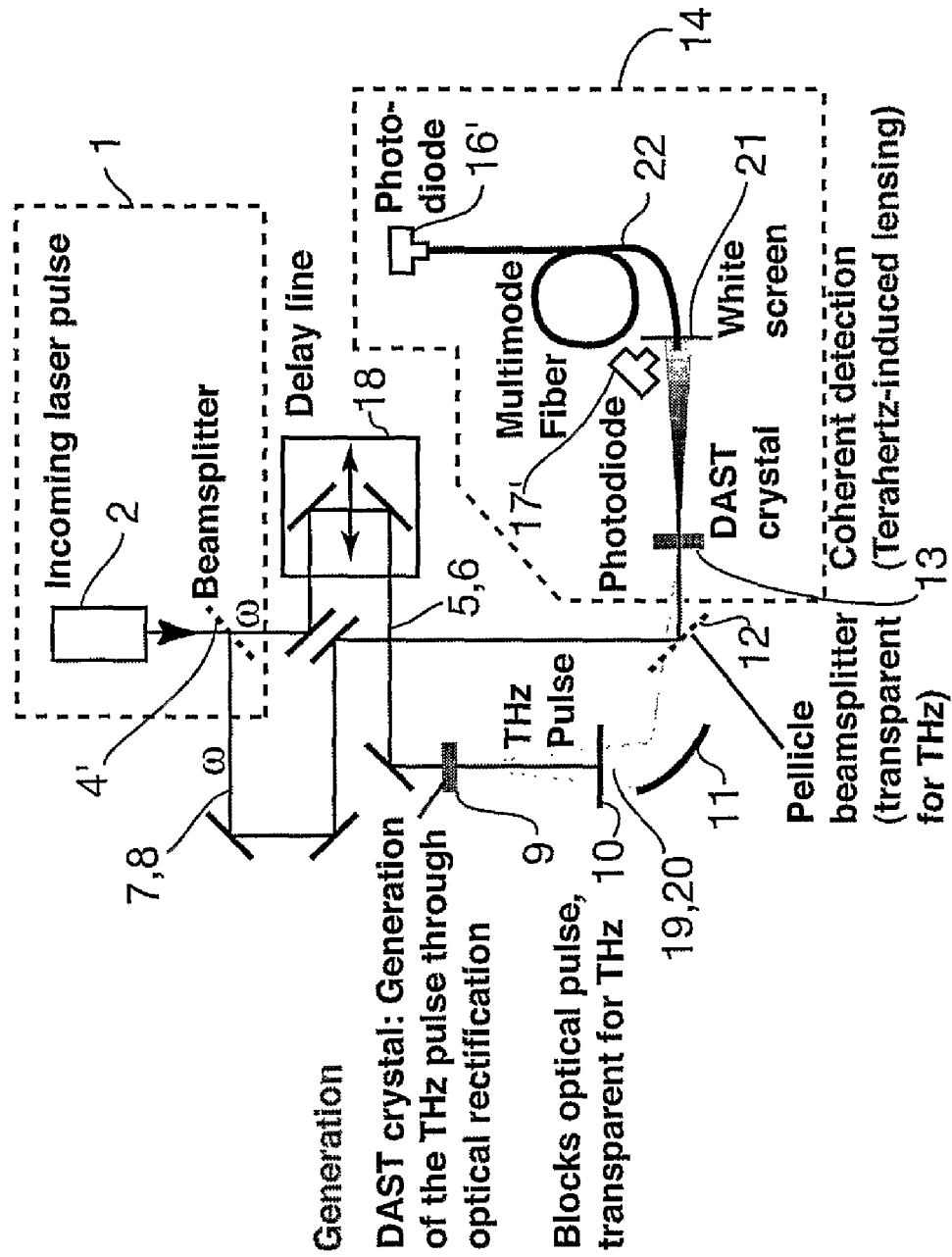
FIG. 8 shows an inventive system using a pump beam at $\omega$ and a probe beam at $\omega$ with generation and detection in DAST

As shown in FIG. 8, the probe beam 7 is projected onto a screen 21. A multimode fiber 22 is coupled to the center of the screen 21 and enables measurement of the intensity of the probe beam in its center by a first photodiode 16' arranged at the other end of the fiber 22. A second photodiode 17' measures the overall intensity of the probe beam 7 on the screen 21 and acts as a reference. The ratio of the signals of the two photodiodes 16, 17 is a measure for the THz-induced lensing and, thus, the amplitude of the THz beam 19.

Results 4.1. Detection in DAST Crystals

Figure 5A:
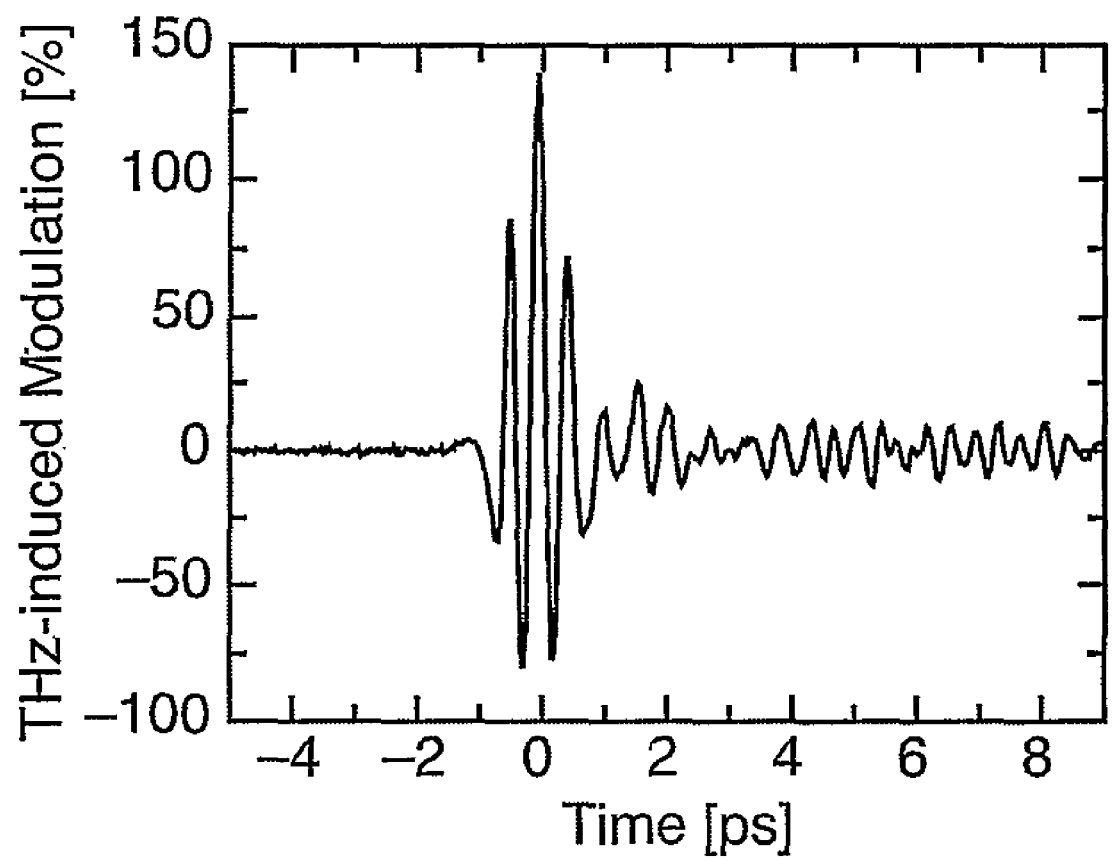
FIGS. 5a+b show a THz pulse generated through optical rectification in a 0.60 mm thick DAST crystal and detected using THz-induced lensing [20] in a 0.69 mm thick DAST crystal, at an optical wavelength of 1.50 µm.

In FIG. 5a+b, we show a THz pulse generated and detected in DAST crystals with 150 fs laser pulses at a wavelength of 1.50 µm and a pulse energy of 25 µJ, e.g. with a setup according to FIG. 8. The time-domain signal FIG. 5a, measured by varying the delay 18, is the relative intensity modulation $m(t) = \Delta I(t)/I_0$ in the center of the probe beam caused by the lensing effect that the THz electric field $E_{THz}(t)$ exerts on the probe beam profile in the far-field after the electro-optic detection crystal 13 (THz-induced lensing [20]). The relation between m(t) and $E_{THz}(t)$ is intrinsically linear for a relative modulation well below unity; the signal presented in FIG. 5a+b however exceeds the linearity range. As an estimation, we calculated the maximum electric field of the THz pulse in the linear regime using Ref. [20] and obtained a value of 50 kV/cm.

A direct comparison of this value with those obtained by other groups in different materials is difficult, since absolute values of the transient THz electric field are often not published. However, the ratio between the induced modulation per pump pulse energy and crystal thickness may serve as a measure for the conversion efficiency. Nagai et al. reported $12(\text{mm mJ})^{-1}$ for their experiment with 1.56 µm pulses in GaAs ($\Delta I/I_0 = 2 \cdot 10^{-5}$, pulse energy 3.4 nJ, 0.5 mm crystal [4]), compared to $93(\text{mm mJ})^{-1}$ in our experiment. Considering that the negative effect of two-photon absorption on the THz amplitude is stronger for the higher energy optical pulses in our setup, one can conclude that the THz generation efficiency using DAST crystals at telecommunication wavelengths is an order of magnitude higher than that using GaAs at comparable wavelengths.

Figure 5B:
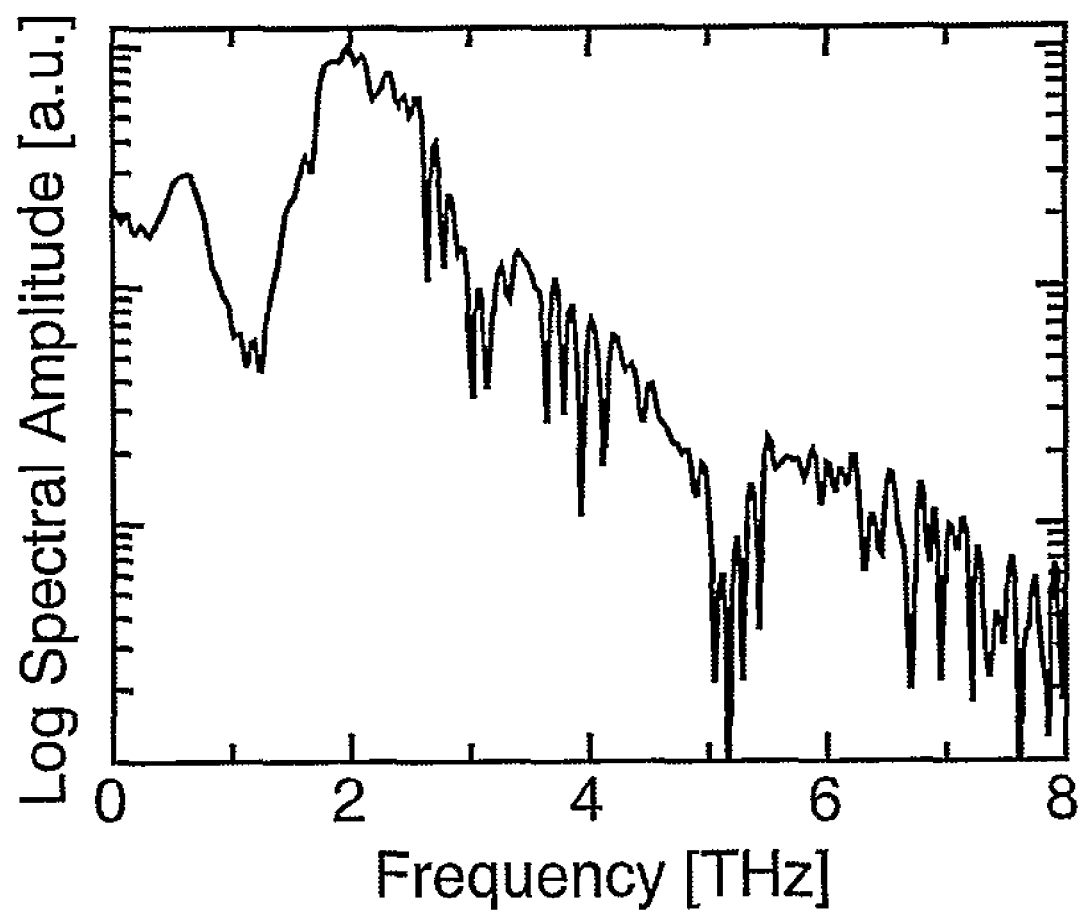
FIG. 5b: Fourier transform of the same THz pulse. Absorption by the residual ambient water vapor leads in time-domain to the oscillation that persists for t>1 ps, in frequency-domain to the numerous dips; thus the effectively emitted THz spectrum is given by the envelope.

The Fourier spectrum of the THz pulse in FIG. 5b extends from 0 to 6.5 THz, where the upper frequency limit is mainly determined by the duration of the optical probe pulse. Absorption of the THz wave in the DAST crystals reduces the amplitude at the resonance frequencies 1.1 THz [14], 3.1 THz, and 5.2 THz [21]. However, the second resonance at 3.1 THz is weak enough not to reduce the amplitude to the noise level, such that a continuous spectrum without gaps is obtained in the central part of the spectrum from 1.3 to 4.8 THz.

Detection in ZnTe Using a Frequency-Doubled Probe Beam

Figure 6A:
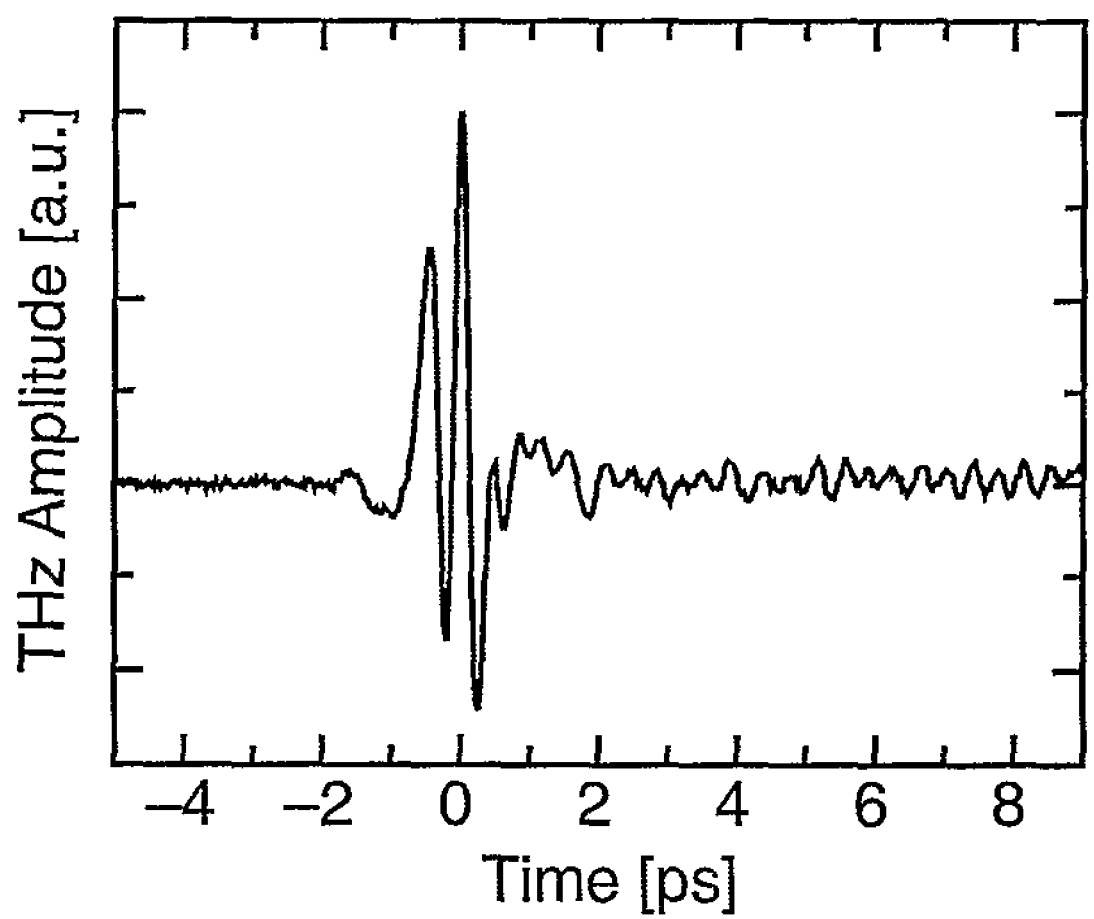
FIGS. 6a+b show a THz pulse generated through optical rectification of 1.5 µm pulses in a 0.60 mm thick DAST crystal and detected by electro-optic sampling in a 0.5 mm thick ZnTe crystal using a frequency-doubled probe beam ($\lambda=0.75$ µm).
Figure 6B:
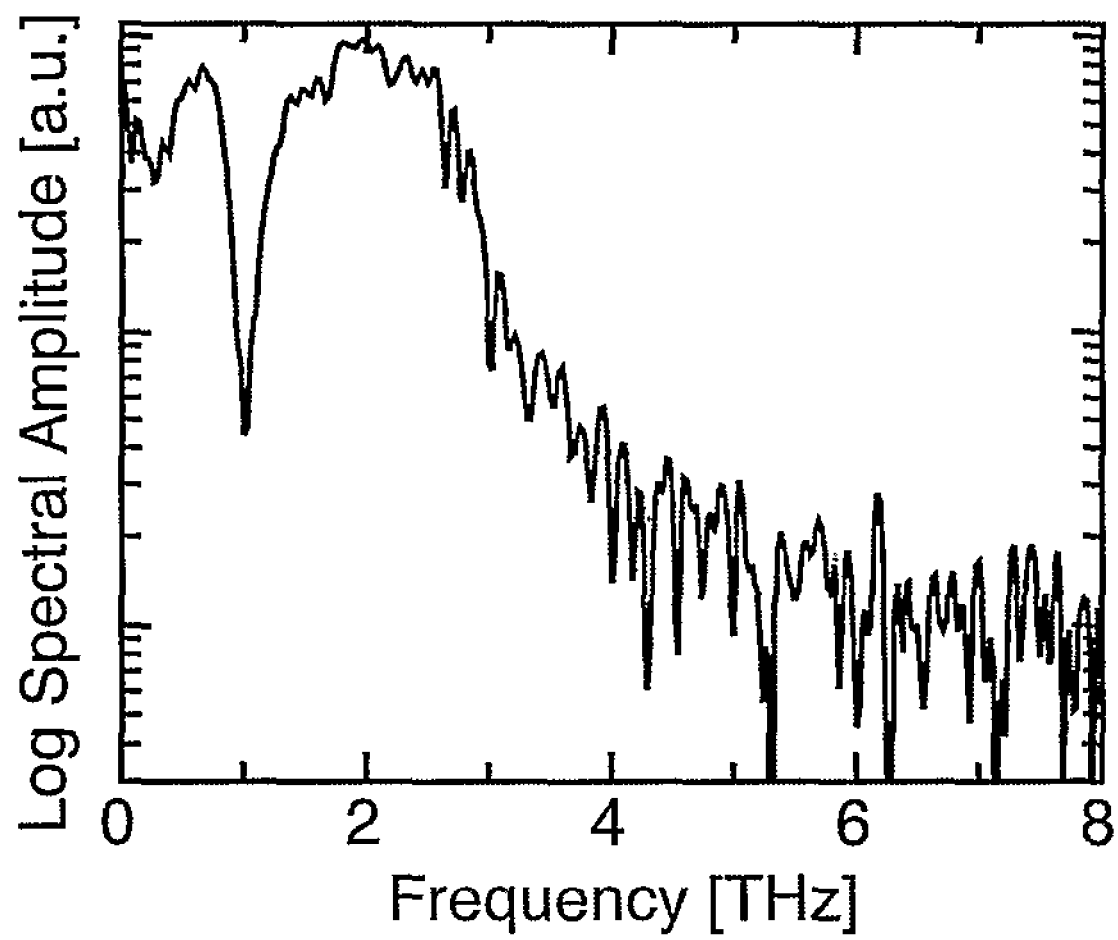
FIG. 6b: Frequency-domain. The effect of water vapor absorption is the same as in FIG. 5.

In FIG. 6a+b we present a measurement of the same THz pulse in time and frequency-domain, detected by EO sampling in a ZnTe crystal with a frequency-doubled probe beam ($\lambda = 0.75$ µm). The spectrum extends from 0 to 4 THz, again with a gap at 1.1 THz due to the phonon resonance in DAST. Here, the upper frequency limit is given by the properties of the detection material, on the one hand since the coherence length becomes shorter than the crystal thickness above 3.5 THz (see FIG. 2), on the other hand due to the THz absorption in ZnTe that strongly increases above 4 THz [16]. The residual velocity-mismatch in ZnTe for the major part of the spectrum leads to a reduction of the maximum THz amplitude compared to that in FIG. 5, such that the linearity range of the detection is not exceeded.

It is remarkable that the observed upper frequency limit of 4 THz lies higher than that measured with e.g., 800 nm probe pulses [2], even though the optimum probe wavelength for ZnTe was considered to be 822 nm so far [3]. This can be explained by the increased coherence length for frequencies above 3 THz at $\lambda = 750$ nm compared to 800 nm (see FIG. 2).

Conclusions

In conclusion, we demonstrated a highly efficient generation and detection of few-cycle THz pulses using optical pulses at a wavelength of 1.5 µm and the nonlinear optical crystal DAST. Its large nonlinear optical susceptiblity can be fully exploited due to a coherence length $l_c$ above 1 mm from 1.5 to 4.5 THz at this wavelength. Alternatively, nearly velocity-matched detection in ZnTe crystals was achieved for a frequency-doubled probe beam, resulting in a continuous spectrum from 1.3 to 4 THz. This is important since the detection by conventional electro-optic sampling in ZnTe is more versatile than by THz-induced lensing as it was used with DAST.

Together with compact and stable femtosecond lasers originally built for the telecommunications industry, DAST-based systems are an efficient and cost-effective alternative for any application of short THz pulses.

6. Further Embodiments

Figure 7:
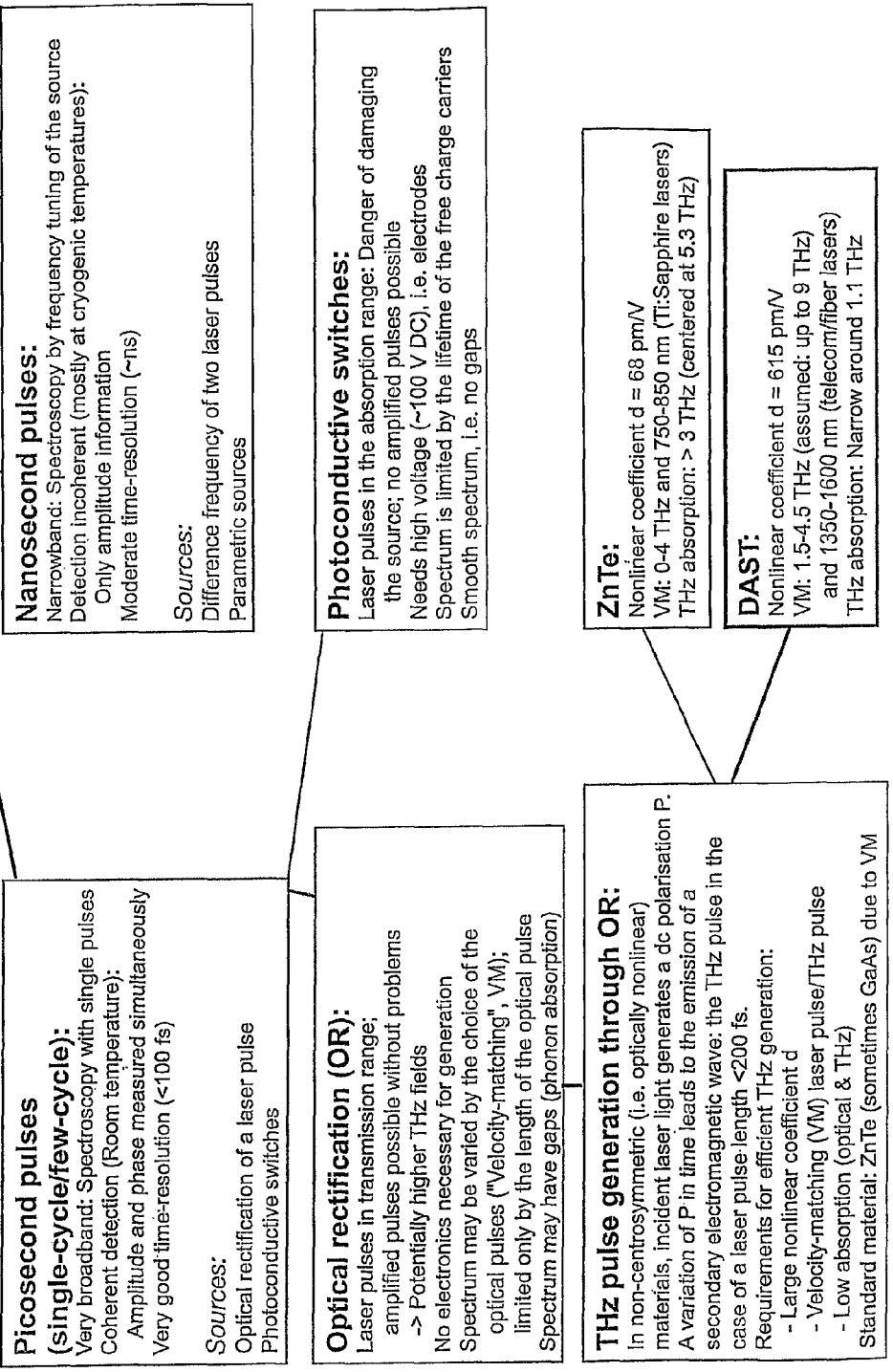
FIG. 7 gives an overview of different processes for THz pulse generation and detection

FIG. 7 gives an overview over different methods for THz generation and detection with their advantages and drawbacks.

Figure 9:
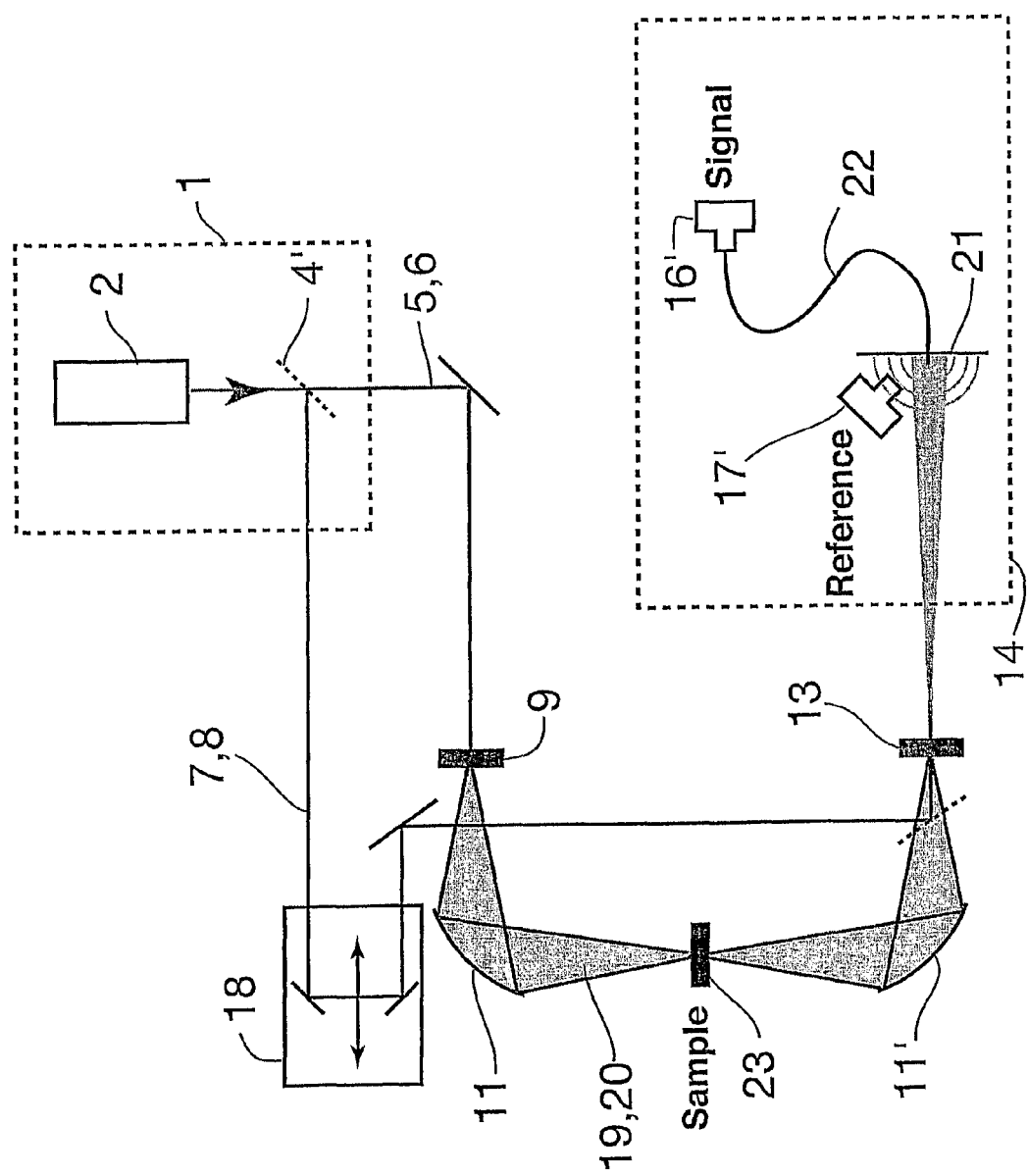
FIG. 9 shows an inventive system with a sample located within the THz beam path.

FIG. 9 shows a system for measuring properties of a sample 23 by THz radiation. The basic setup corresponds to FIG. 4 or 8, for example, with the difference that the delay is arranged in the probe beam path. By a first mirror 11, the Terahertz beam 19 is directed and focused onto the sample 23. A second mirror 11' serves for directing and focusing the Terahertz beam 19 onto the detection crystal 13. The sample 23 may be moved with respect to the Terahertz beam 19 (indicated by the arrows) in order to scan the sample in space, e.g. along a line or in two dimensions. It is also possible to vary the Terahertz beam path 20, e.g. by adjusting the mirrors 11, 11', in order to scan the Terahertz beam 19 over the sample. Additionally or alternatively, the delay 18 may be varied and a delay-dependent signal acquired. This signal corresponds to the amplitude of the Terahertz beam as a function of time, and yields the Terahertz spectrum after Fourier transformation. Consequently, spectral information, optionally spatially resolved, may be retrieved.

Figure 10:
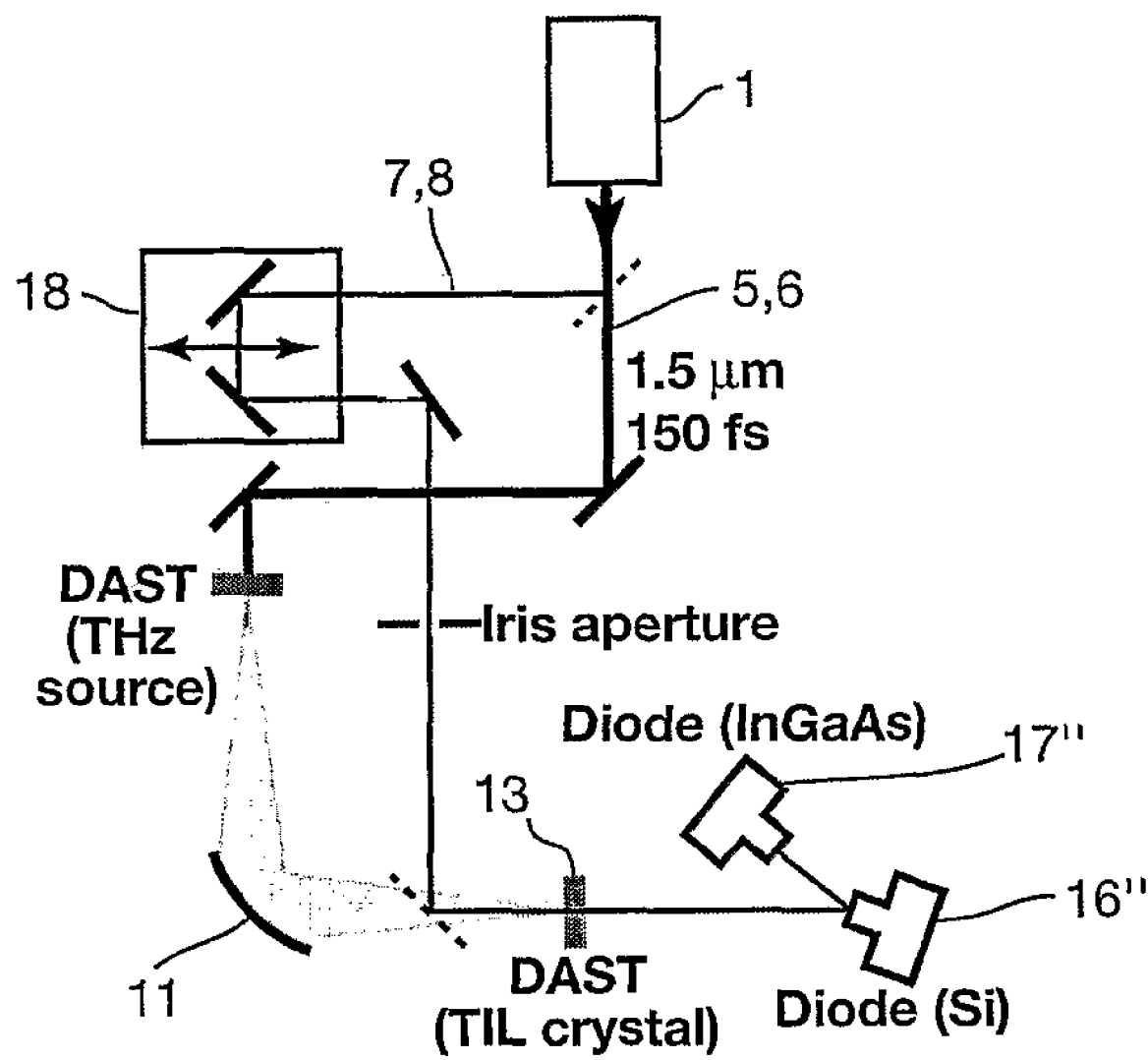
FIG. 10 shows an alternative method to detect THz radiation by THz induced lensing.

FIG. 10 shows an alternative method to detect THz radiation by THz induced lensing in a nonlinear optical crystal 13, e.g. in a DAST crystal. The method is based on two-photon absorption of a probe pulse in a standard photodiode 16", e.g. a silicon photodiode or any other detection material with no or reduced sensitivity at the probe wavelength. The change in the spatial probe pulse profile caused by terahertz-induced lensing leads to a variation of the diode signal that is induced by two-photon absorption even though the total pulse energy has remained constant. This variation is proportional to the terahertz electric field.

The experimental setup for the coherent detection of terahertz pulses (the Terahertz beam path 20 is indicated by a shade of gray) generally corresponds to FIG. 8 (with the exception of the location of the delay line). The THz pulses are generated by optical rectification in a first nonlinear optical crystal 9, e.g. DAST, here pumped by a 1.5 µm, 150 fs pump beam 5 for example. The thin line represents the beam path 7 of the probe pulse that is focused by the THz electric field in the second nonlinear crystal 13, e.g. also DAST, through Terahertz-induced lensing (TIL). The different intensity distribution on the Si diode 16' leads to a change in the two-photon absorption within the Si photodiode that is proportional to the THz field. The further photodiode 17", e.g. a InGaAs photodiode or any other photosensitive material with normal sensitivity at the pump wavelength, is used as a reference to correct for pulse energy fluctuations.

The method is simple and robust and is suited for the measurement of the terahertz-induced lensing effect, also in other materials than DAST, and may also be used for the coherent detection of few-cycle terahertz pulses in general.

Figure 11A:
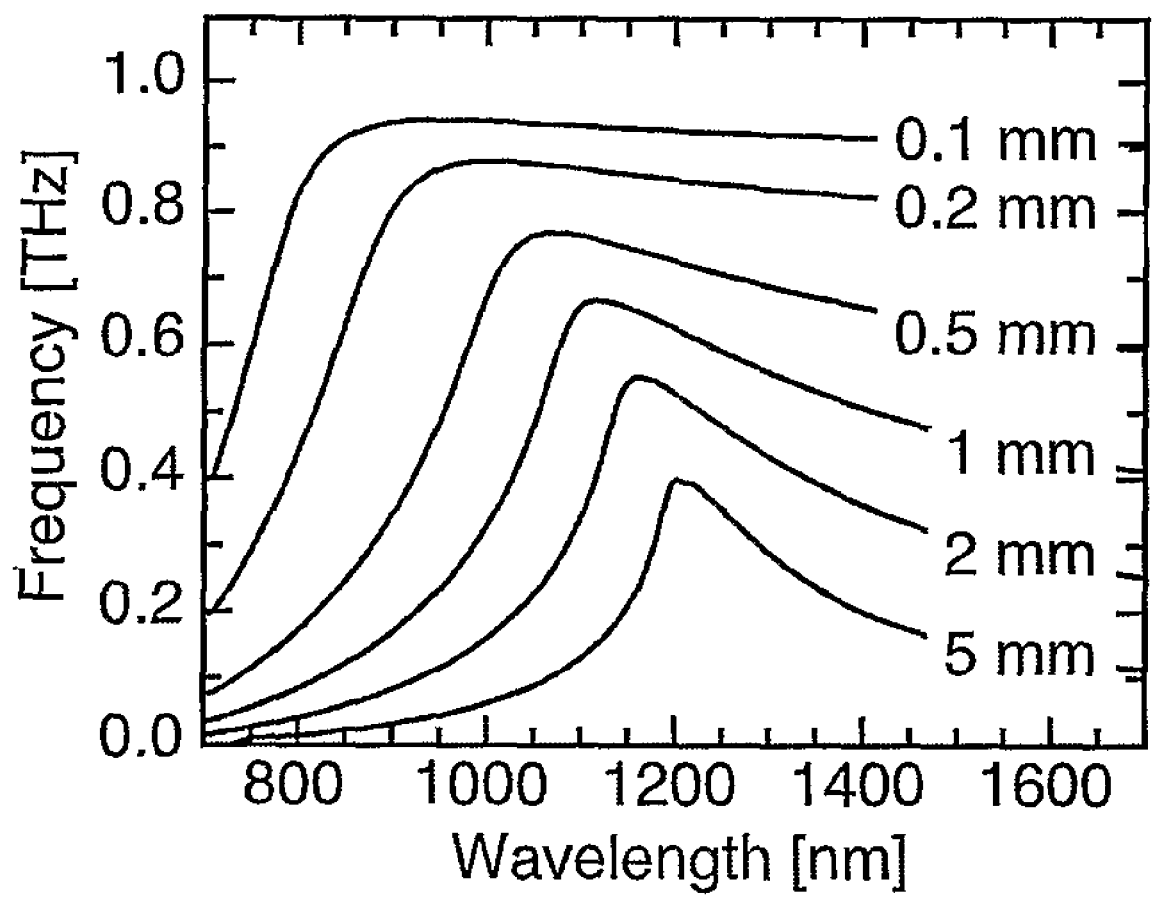
FIG. 11a+b show a contour plot of $L_{max}$, the maximum of the effective generation length $L_{gen}(\omega,\lambda,z)$ when the actual crystal length z is varied, for DAST using $_\chi$OR111 or r111, respectively, for THz frequencies of 0-1 THz (FIG. 11a) and more than 1 THz (FIG. 11b). The thick line represents 0.5 mm, the line spacing equals 0.1 mm throughout.
Figure 11B:
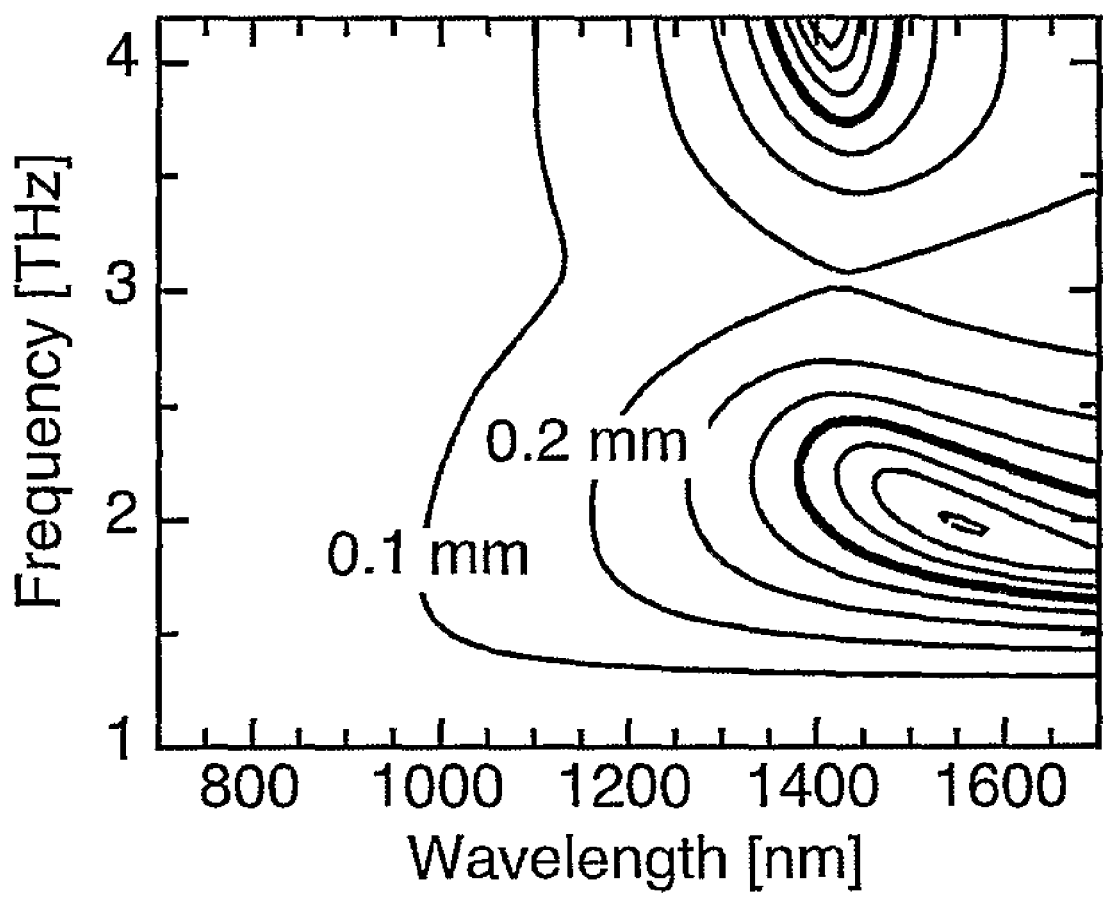

FIG. 11a+b show a contour plot of the maximum effective length $L_{max}$ for DAST using $\chi$OR111 or r111, respectively, for THz frequencies of 0-1 THz (FIG. 11a) and more than 1 THz (FIG. 11b). $L_{max}$ is a generalization of the coherence length $l_c$ that incorporates additionally absorption effects within the material [15]. The thick line in FIG. 11b represents 0.5 mm, the line spacing equals 0.1 mm throughout.

Figure 12A:
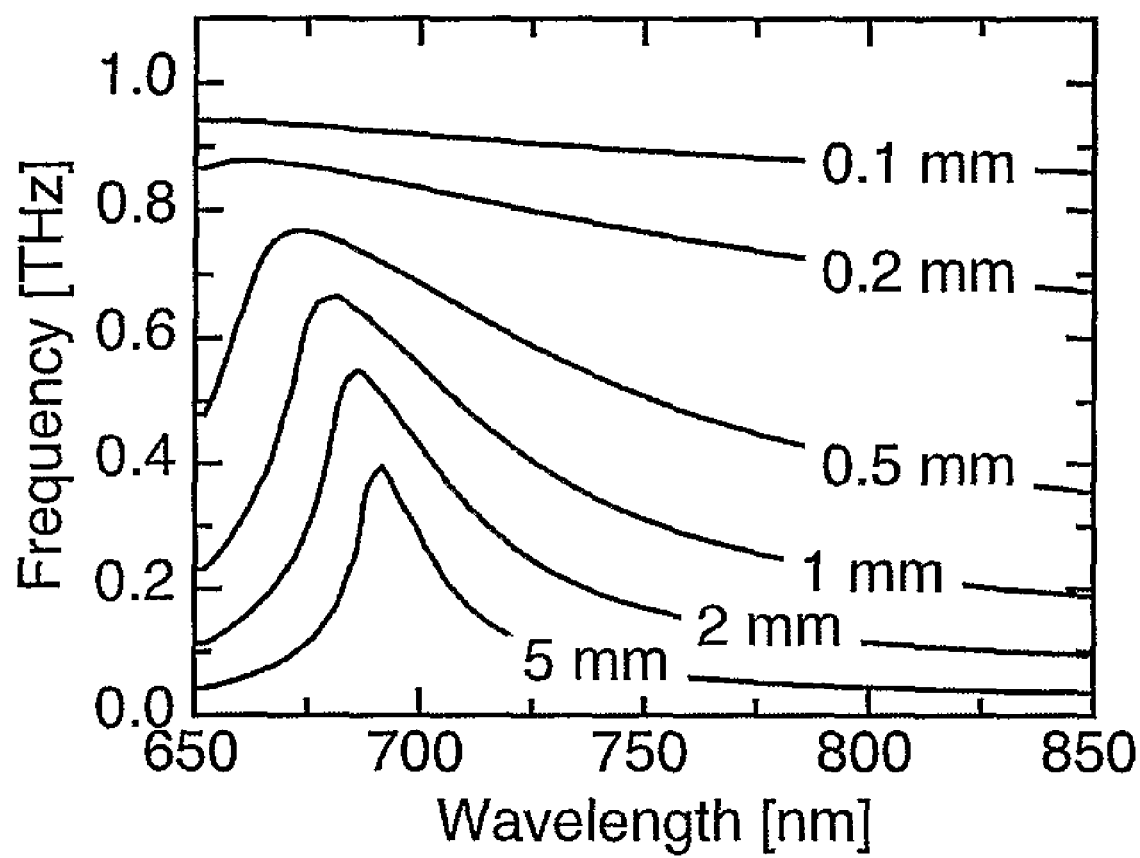
FIG. 12a+b show a contour plot of $L_{max}$, the maximum of the effective generation length $L_{gen}(\omega,\lambda,z)$ when the actual crystal length z is varied, for DAST using $_\chi$OR122 or r221, respectively, for THz frequencies of 0-1 THz (FIG. 12a) and more than 1 THz (FIG. 12b).
Figure 12B:
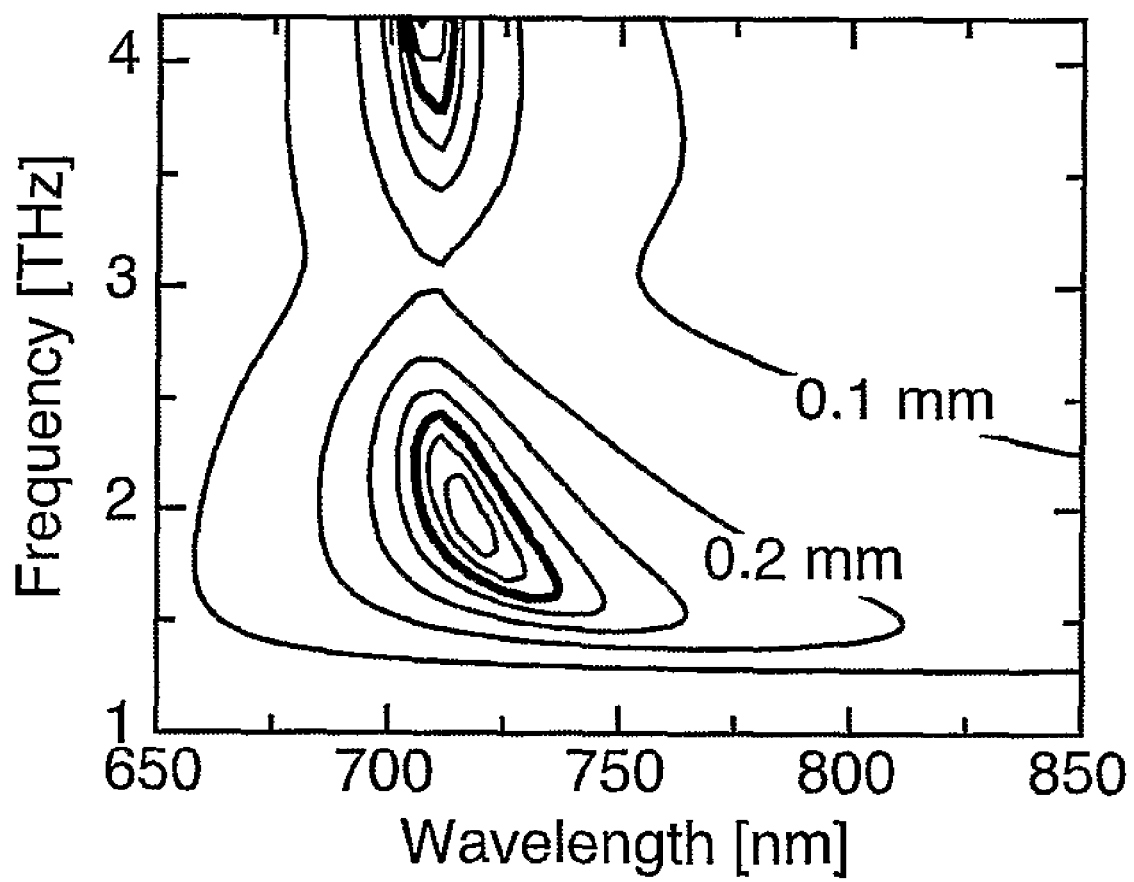

FIG. 12a+b is analog to FIG. 11a+b, but showing $L_{max}$ for DAST using $\chi$OR122 or $r_{221}$, respectively, i.e., the polarization of the optical wave is parallel to the crystal b-(or 2-)axis, whereas the THz field is still polarized along the a-(or 1-)axis.

One finds that the emitted THz field E varies with the real crystal length z proportional to the following factor $L_{gen}(\omega, \lambda, z)$ which may thus be regarded as an effective crystal length for the generation of terahertz pulses. Since the optical absorption coefficient $\alpha_0$ is negligibly small, the same proportionality applies to the coherent detection by electro-optic sampling in the same material.

$$L_{gen}(\omega, \lambda, z) = \left( \frac{1 + e^{-\alpha(\omega)z} - 2e^{-\alpha(\omega)z/2} \cos[n(\omega) - n_g(\lambda)]}{[\alpha(\omega)/2]^2 + [\omega/c]^2[n(\omega) - n_g(\lambda)]} \right)^{1/2}$$

For nonzero absorption coefficient $\alpha(\omega) \neq 0$ and a dispersive material, where the indices n and $n_g$ vary with the angular terahertz frequency $\omega$ and optical wavelength $\lambda$, respectively, $L_{gen}$ reaches a maximum as a function of the crystal thickness z for fixed values of $\omega$ and $\lambda$.

FIGS. 11a+b and 12a+b present calculations of these maximum values of Lgen for DAST for two different combinations of polarisations of the electric fields of the THz wave and the optical, respectively. FIG. 11a+b: Both fields are polarized along the crystal a-axis (or 1-axis). FIG. 12a+b: The THz field is polarized along the a (or 1)-axis, the optical field along the b (or 2)-axis.

The graphs may be interpreted as follows. The larger the plotted value, the more efficient the THz generation process can be (respectively the more sensitive the detection) for the given combination of $\omega$ and $\lambda$. However, the crystal length must be chosen adequately. As a rule of thumb, it ought to be 1.6 to 2.2 times larger than the plotted maximum value of $L_{gen}(\omega,\lambda,z)$.

If the crystal is shorter, its potential is not fully used, if it is longer, the emitted amplitude might already decrease.

Example: One is interested in a THz amplitude between, say, 2.0 and 2.5 THz. The plotted value in FIG. 11a+b is about constant and at maximum for $\lambda$~1400 nm: $L_{gen}$~0.5 mm. Thus it is favorable to use a 0.8-1.1 mm thick crystal and an optical wavelength of 1400 nm.

Several combinations of the optical wavelength $\lambda$ and THz frequency v with enhanced THz emission could be identified. Within the tuning range of Ti:Sapphire lasers, velocity-matched THz generation is achieved using the nonlinear coefficient $\chi^{(2)}122$ and a pump wavelength of 700 to 740 nm (see FIG. 12a+b). Of primary technological importance is that telecom wavelengths $\lambda$ around 1500 nm are velocity-matched to frequencies between 1.5 THz and 2.7 THz if the largest nonlinear coefficient $\chi^{(2)}$ 111 is used (FIG. 11a+b).

Using DAST crystals of less than 0.7 mm thickness for generation and detection, we have demonstrated a THz-induced modulation of 140 percent in a nominally linear regime (see FIG. 5a). With the advent of compact and stable femtosecond lasers at 1.5 to 1.56 µm (e.g. Erbium-doped fiber lasers), highly efficient and cost-effective THz systems may be developed using DAST as the THz emitter. Higher frequencies (3.3 THz to 6.7 THz) are most efficiently generated using $\lambda$ near 1350 nm. These results demonstrate the considerable potential of DAST for THz applications in general and how it can be fully exploited.

REFERENCE AND LINKS

1. B. Ferguson and X.-C. Zhang, "Materials for terahertz science and technology," Nature Materials 1, 26-33 (2002)
2. A. Nahata, A. S. Weling, and T. F. Heinz, "A wideband coherent terahertz spectroscopy system using optical rectification and electro-optic sampling," Appl. Phys. Lett. 69, 2321-2323 (1996)
3. Q. Wu and X.-C. Zhang, "Design and Characterization of Traveling-Wave Electrooptic Terahertz Sensors," IEEE J. Sel. Top. Quantum Electron. 2, 693-700 (1996).
4. M. Nagai, K. Tanaka, H. Ohtake, T. Bessho, T. Sugiura, T. Hirosumi, and M. Yoshida, "Generation and detection of terahertz radiation by electro-optical process in GaAs using 1.56 □m fiber laser pulses," Appl. Phys. Lett. 85, 3974-3976 (2004).
5. Ch. Bosshard, K. Sutter, Ph. Prêtre, J. Hulliger, M. Flörsheimer, P. Kaatz, and P. Günter, "Organic Nonlinear Optical Materials," Advances in Nonlinear Optics Vol. 1, Gordon and Breach, Amsterdam (1995)
6. L. M. Hayden, A. M. Sinyukov, M. R. Leahy, J. French, P. Lindahl, W. N. Herman, R. J. Twieg, and M. He, "New Materials for Optical Rectification and Electrooptic Sampling of Ultrashort Pulses in the Terahertz Regime," J. Polym. Sci. Part B Polym. Phys. 41, 2492-2500 (2003)
7. F. Pan, G. Knöpfle, Ch. Bosshard, S. Follonier, R. Spreiter, M. S. Wong, and P. Günter, "Electro-optic properties of the organic salt 4-N,N-dimethylamino-4'-N'-methyl-stilbazolium tosylate," Appl. Phys. Lett. 69, 13-15 (1996)
8. A. Schneider, I. Biaggio, and P. Günter, "Optimized generation of THz pulses via optical rectification in the organic salt DAST," Opt. Commun. 224, 337-341 (2003)
9. H. J. Bakker, G. C. Cho, H. Kurz, Q. Wu, and X.-C. Zhang, "Distortion of terahertz pulses in electro-optic sampling," J. Opt. Soc. Am. B 15, 1795-1801 (1998).
10. Q. Wu and X.-C. Zhang, "Free-space electro-optic sampling of terahertz beams," Appl. Phys. Lett. 67, 3523-3525 (1995)
11. P. Y. Han, M. Tani, F. Pan, and X.-C. Zhang, "Use of the organic crystal DAST for terahertz beam applications," Opt. Lett. 25, 675-677 (2000)
12. Q. Wu, T. D. Hewitt, and X.-C. Zhang, "Two-dimensional electro-optic imaging of THz beams," Appl. Phys. Lett. 69, 1026-1028 (1996)
13. J. Shan, A. S. Weling, E. Knoesel, L. Bartels, M. Bonn, A. Nahata, G. A. Reider, and T. F. Heinz, "Single-shot measurement of terahertz electromagnetic pulses by use of electro-optic sampling," Opt. Lett. 25, 426-428 (2000)
14. M. Walther, K. Jensby, S. R. Keiding, H. Takahashi, and H. Ito, "Far-infrared properties of DAST," Opt. Lett. 25, 911-913 (2000)

15. A. Schneider, M. Neis, M. Stillhart, B. Ruiz, R. Khan, and P. Gunter, "Generation of terahertz pulses through optical rectification in organic DAST crystals: Theory and experiment," J. Opt. Soc. Am. B 23, 1822-1835(2006)
16. G. Gallot, J. Zhang, R. W. McGowan, T.-I. Jeon, and D. Grischkowsky, "Measurements of the THz absorption and dispersion of ZnTe and their relevance to the electro-optic detection of THz radiation," Appl. Phys. Lett. 74, 3450-3452 (1999)
17. M. Schall, M. Walther, and P. Uhd Jepsen, "Fundamental and second-order phonon processes in CdTe and ZnTe," Phys. Rev. B 64, 094301 (2001)
18. T. R. Sliker and J. M. Jost, "Linear Electro-Optic Effect and Refractive Indices of Cubic ZnTe," J. Opt. Soc. Am. 56, 130-131 (1966)
19. K. Sato and S. Adachi, "Optical properties of ZnTe," J. Appl. Phys. 73, 926-931 (1993)
20. A. Schneider, I. Biaggio, and P. Günter, "Terahertz-induced lensing and its use for the detection of terahertz pulses in a birefringent crystal," Appl. Phys. Lett. 84, 2229-2231 (2004)
21. T. Taniuchi, S. Okada, and H. Nakanishi, "Widely tunable terahertz-wave generation in an organic crystal and its spectroscopic application," J. Appl. Phys. 95, 5984-5988 (2004)
22. Z. Yang, L. Mutter, M. Stillhart, B. Ruiz, S. Aravazhi, M. Jazbinsek, A. Schneider, V. Gramlich, and P. Gunter, "Large-size bulk and thin-film stilbazolium-salt single crystals for nonlinear optics and THz generation," Advanced Functional Materials, in press (2007), and U.S. Provisional 60/845,566, filed 18 Sep. 2006
23. Z. Yang, S. Aravazhi, A. Schneider, P. Seiler, M. Jazbinsek, and P. Gunter, "Synthesis and Crystal Growth of Stilbazolium Derivatives for Second-Order Nonlinear Optics," Advanced Functional Materials 15, 1072-1076(2005)
24. B. Ruiz, Z. Yang, V. Gramlich, M. Jazbinsek, and P. Günter, "Synthesis and crystal structure of a new stilbazolium salt with large second-order optical nonlinearity," Journal of Materials Chemistry 16, 2839-2842 (2006)

What is claimed is:

1. A broadband Terahertz radiation generation and detection system comprising:
    a light source for generating a pump beam and a probe beam each comprising light pulses in the optical range having a pulse duration in the picosecond- or sub-picosecond range, the light source comprising a laser;
    a first nonlinear optical crystal arranged in a pump beam path, wherein a Terahertz beam is generated upon exposure of the first nonlinear optical crystal with the pump beam;
    a second nonlinear optical crystal arranged in a probe beam path and in a Terahertz beam path, wherein optical properties of the probe beam are altered when the second nonlinear optical crystal is exposed with the probe beam and the Terahertz beam;
    a detector for detecting predetermined optical parameters of the probe beam,
    wherein the light source generates the pump beam with a central frequency $\omega$ corresponding to the central frequency of the laser and generates the probe beam with a central frequency $2\omega$ by second harmonic generation with a further nonlinear optical crystal.

2. The system according to claim 1, wherein the first nonlinear optical crystal is a stilbazolium salt crystal.

3. The system according to claim 1, wherein the first nonlinear optical crystal is a DAST (4-N,N-dimethylamino-4'-N'-methyl stilbazolium tosylate) crystal.

4. The system according to claim 1, wherein the first nonlinear optical crystal is a DSMOS (4-N,N-dimethylamino-4'-N'-methyl stilbazolium p-methoxybenzenesulfonate) or a DSTMS (4-N,N-dimethylamino-4'-N'-methyl stilbazolium 2,4,6 trimethylbenzenesulfonate) crystal.

5. The system according to claim 1, wherein the second nonlinear optical crystal is a ZnTe (zinc telluride) crystal.

6. The system according to claim 1, wherein a central wavelength of the light pulses generated by the laser is in the range between 1.0 and 1.7 µm.

7. The system according to claim 1, wherein the first nonlinear optical crystal is a DAST (4-N,N-dimethylamino-4'-N'-methyl stilbazolium tosylate) crystal, the pump beam has a first wavelength between 1.3 and 1.6 µm, and the second optical crystal is a ZnTe (zinc telluride) crystal.

8. The system according to claim 1, wherein the first nonlinear optical crystal is a DAST (4-N,N-dimethylamino-4'-N'-methyl stilbazolium tosylate) crystal, the pump beam has a first wavelength between 1.4 and 1.7 µm and wherein the pump beam is directed onto the first nonlinear optical crystal such that its polarization has a component in the same direction as the main (a-) axis of the first nonlinear optical crystal.

9. The system according to claim 1, wherein the light source comprises a pulsed fiber laser.

10. The system according to claim 1, wherein optical properties of the first nonlinear optical crystal, preferably its material and orientation, and the first wavelength of the pump beam are chosen such that velocity-matching conditions between the pump beam and the Terahertz radiation are fulfilled.

11. The system according to claim 1, wherein optical properties of the second nonlinear optical crystal, preferably its material and orientation, and the wavelength of the probe beam are chosen such that velocity-matching conditions between the probe beam and the Terahertz radiation are fulfilled.

12. The system according to claim 1, wherein the coherence length of the Terahertz radiation and the pump beam in the first nonlinear optical crystal is larger than the thickness of the first nonlinear optical crystal in the direction of propagation of the Terahertz beam and the pump beam.

13. The system according to claim 1, wherein the pulse duration of the pump light pulses is less than 1 ps.

14. The system according to claim 1, further comprising a variable delay positioned in at least one of the paths of the pump beam, and the probe beam.

15. The system according to claim 1, further comprising means for moving a sample and/or the Terahertz beam with respect to one another.

16. The system according to claim 1, wherein the second nonlinear crystal is configured such that the polarization state of the probe beam passing through the second nonlinear crystal is altered in presence of the Terahertz beam, preferably by electro-optic sampling, and wherein the detection means are configured to detect polarization changes in the probe beam.

17. The system according to claim 1, wherein the second nonlinear crystal is configured such that the spatial intensity distribution of the probe beam passing through the second nonlinear crystal is altered in the presence of the Terahertz beam, preferably by Terahertz induced lensing, and wherein the detection means are configured to detect changes in the spatial intensity distribution.

18. The system according to claim 17, wherein the detection means comprise a semiconductor photodiode having no or small sensitivity at the wavelength of the probe beam but a given sensitivity at the second harmonic of the wavelength of the probe beam.

19. The system according to claim 1, wherein a central wavelength of the light pulses generated by the laser is in the range between 1.3 and 1.6 µm.

20. The system according to claim 1, wherein the light source comprises a dichroic mirror designed to divide the pump beam and the probe beam from one another, wherein the dichroic mirror is arranged in a beam path of the laser behind the further nonlinear optical crystal as seen in the direction of light propagation.

21. The system according to claim 1, wherein the material of the first nonlinear optical crystal is different from the material of the second nonlinear optical crystal.

22. Method for broadband Terahertz generation and detection, comprising the following steps:
providing a laser;
generating a pump beam with a central frequency w corresponding to the central frequency of the laser and generating a probe beam with a central frequency 2ω by second harmonic generation, the pump beam and the probe beam each comprising light pulses in the optical or infrared range having a pulse duration in the picosecond- or sub-picosecond range,
exposing a first nonlinear optical crystal with the pump beam in order to generate a Terahertz beam;
exposing a second nonlinear optical crystal with the probe beam and the Terahertz beam in order to alter optical properties of the probe beam in presence of the Terahertz beam;
detecting predetermined optical parameters of the probe beam.

23. Method according to claim 22, further comprising directing the Terahertz beam onto a sample.

24. Method according to claim 22, further comprising adapting the lengths of the optical paths of the probe beam and the Terahertz beam to one another in order to achieve coherent detection within the second nonlinear crystal.

25. Method according to claim 22, wherein the first and second wavelength, the orientation of the polarizations of the pump beam and the probe beam with respect to the first and/or second nonlinear crystal and the optical properties of the first and second nonlinear optical crystal are chosen such that velocity-matching conditions between the pump beam and the Terahertz radiation in the first nonlinear optical crystal and between the pump beam and the Terahertz radiation in the second nonlinear optical crystal are fulfilled.

26. Method according to claim 22, wherein the first nonlinear optical crystal is a DAST (4-N,N-dimethylamino-4'-N'-methyl stilbazolium tosylate) crystal, the pump beam has a first wavelength between 1.4 and 1.7 µm and wherein the pump beam is directed onto the first nonlinear optical crystal such that its polarization has a component in the same direction as the main (a-) axis of the first nonlinear optical crystal.

27. Method according to claim 22, wherein the first nonlinear optical crystal is a DAST (4-N,N-dimethylamino-4'-N'-methyl stilbazolium tosylate) crystal, the pump beam has a first wavelength between 1.3 and 1.6 µm, and the second optical crystal is a ZnTe (zinc telluride) crystal.

28. Method according to claim 22, wherein the pulse duration of the light pulses is less than 1 ps.

29. Method according to claim 22, further comprising positioning a variable delay in at least one of the paths of the pump beam, and the probe beam.

30. Method according to claim 29, further comprising varying the delay, acquiring a delay dependent signal and generating a spectrum of the Terahertz pulse from said delay dependent signal.

31. Method according to claim 22, further comprising moving the sample and/or the Terahertz beam with respect to one another, acquiring a position dependent signal, and generating an image of the sample from said position dependent signal.

* * * * *